(12) United States Patent
Facchini

(10) Patent No.: US 10,487,345 B2
(45) Date of Patent: Nov. 26, 2019

(54) METHODS FOR MAKING AND USING POLYNUCLEOTIDE SEQUENCES IN THE SYNTHESIS OF ALKALOID COMPOUNDS

(71) Applicant: EPIMERON INC., Calgary (CA)

(72) Inventor: Peter James Facchini, Calgary (CA)

(73) Assignee: Epimeron Inc., Calgary, Alberta (CA)

( * ) Notice: Subject to any disclaimer, the term of this patent is extended or adjusted under 35 U.S.C. 154(b) by 26 days.

(21) Appl. No.: 15/307,616

(22) PCT Filed: Apr. 27, 2015

(86) PCT No.: PCT/CA2015/050346
§ 371 (c)(1),
(2) Date: Oct. 28, 2016

(87) PCT Pub. No.: WO2015/164960
PCT Pub. Date: Nov. 5, 2015

(65) Prior Publication Data
US 2017/0058305 A1    Mar. 2, 2017

Related U.S. Application Data

(60) Provisional application No. 61/985,742, filed on Apr. 29, 2014, provisional application No. 62/094,376, filed on Dec. 19, 2014.

(51) Int. Cl.
| | | |
|---|---|---|
| *C12P 17/12* | (2006.01) | |
| *C12N 9/02* | (2006.01) | |
| *C12N 1/20* | (2006.01) | |
| *C12N 15/00* | (2006.01) | |
| *C12N 1/14* | (2006.01) | |
| *C07H 21/04* | (2006.01) | |
| *C12N 15/81* | (2006.01) | |
| *C12N 15/10* | (2006.01) | |
| *C12N 15/63* | (2006.01) | |

(Continued)

(52) U.S. Cl.
CPC ............ *C12P 17/12* (2013.01); *C12N 9/0071* (2013.01); *C12N 15/1082* (2013.01); *C12N 15/81* (2013.01); *C12Y 201/01* (2013.01); *C12N 15/1096* (2013.01); *C12N 15/63* (2013.01); *C40B 10/00* (2013.01); *C40B 20/00* (2013.01)

(58) Field of Classification Search
None
See application file for complete search history.

(56) References Cited

U.S. PATENT DOCUMENTS 9,534,241 B2 * 1/2017 Smolke .................... C12P 17/18
2008/0176754 A1 * 7/2008 Smolke .................... C12P 17/12
506/4

OTHER PUBLICATIONS

Desgagne-Penix, I. et al., "Integration of deep transcriptome and proteome analyses reveals the components of alkaloid metabolism in opium poppy cell cultures", BMC Plant Biology, Biomed Central, London, GB, vol. 10, No. 1, p. 252, Nov. 18, 2010.

(Continued)

*Primary Examiner* — Yong D Pak
(74) *Attorney, Agent, or Firm* — Bereskin & Parr LLP/S.E.N.C.R.L.,s.r.l.; Micheline Gravelle

(57) ABSTRACT

Novel methods that may be used for the manufacture of plant alkaloid compounds and novel polynucleotide compounds are provided. The plant alkaloid compounds are useful as medicinal compounds.

Figure 1:
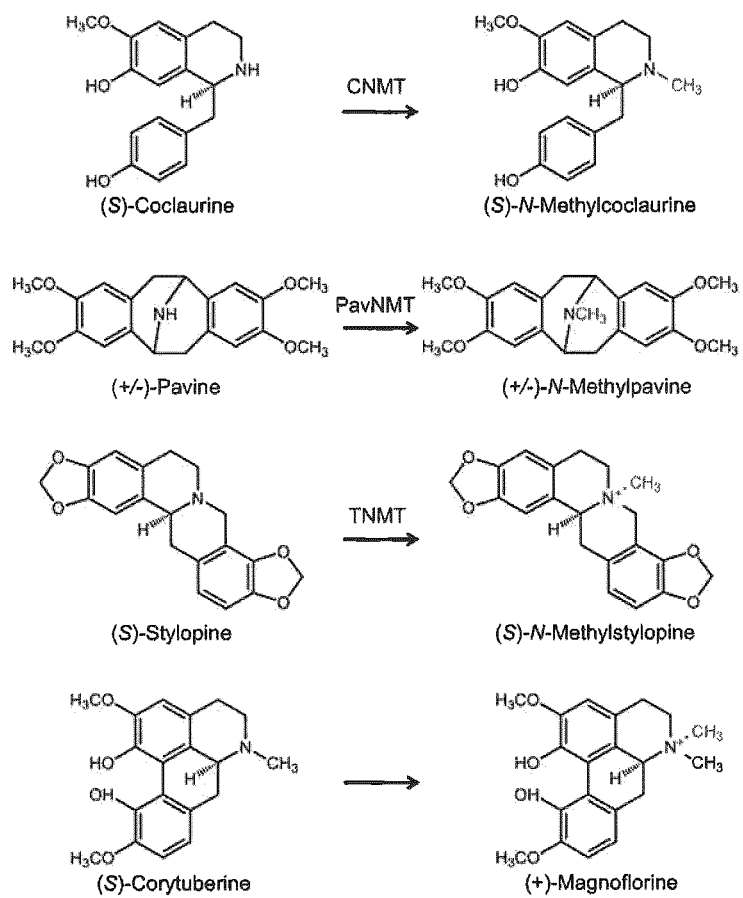

12 Claims, 10 Drawing Sheets
Specification includes a Sequence Listing.

(51) Int. Cl.
    *C40B 10/00*    (2006.01)
    *C40B 20/00*    (2006.01)

(56) References Cited

OTHER PUBLICATIONS

Farrow, S.C. et al., "Transcript and metabolite profiling in cell cultures of 18 plant species that produce benzylisoquinoline alkaloids", Phytochemistry, vol. 77, p. 79-88, Feb. 23, 2012.
Fossati, E. et al., "Reconstitution of a 10-gene pathway for synthesis of the plant alkaloid dihydrosanguinarine in *Saccharomyces cerevisiae*", Nature Communications, vol. 5, p. 1-11, Feb. 11, 2014.
Sato, F. et al., "Microbial production of isoquinoline alkaloide as plant secondary metabolites based on metabolic engineering research", Proceedings of the Japan Academy, Series B, vol. 89, No. 5, p. 165-182, Jan. 1, 2013.
Leonard, E. et al. "Opportunities in metabolic engineering to facilitate scalable alkaloid production", Nature Chemical Biology, vol. 5, No. 5, p. 292-300 (2009).
Xiao, M. et al. "Transcriptome analysis based on next-generation sequencing of non-model plants producing specialized metabolites of biotechnological interest", Journal of Biotechnology, vol. 166, p. 122-134 (2013).

* cited by examiner

ND USING
METHODS FOR MAKING AND USING POLYNUCLEOTIDE SEQUENCES IN THE SYNTHESIS OF ALKALOID COMPOUNDS

RELATED APPLICATIONS

This application is a national phase entry application of Patent Cooperation Treaty Application No. PCT/CA2015/050346, which claims the benefit under 35 USC § 119(e) from U.S. Provisional Patent Application No. 61/985,742 filed on Apr. 29, 2014 and U.S. Provisional Patent Application No. 62/094,376, filed on Dec. 19, 2014, all of which are incorporated by reference herein in their entirety.

FIELD OF THE DISCLOSURE

The compositions and methods disclosed herein relate to alkaloid compounds and to processes for manufacturing the same. More particularly, the present disclosure relates to plant alkaloids, and methods for making such alkaloids using improved polynucleotide sequences.

BACKGROUND OF THE DISCLOSURE

The following paragraphs are provided by way of background to the present disclosure. They are not however an admission that anything discussed therein is prior art or part of the knowledge of persons skilled in the art.

Plants are capable of producing alkaloid compounds in small amounts. In general, these alkaloid compounds are relatively complex organic molecules, containing mostly basic nitrogen atoms. The in planta biosynthesis of an alkaloid compound involves the occurrence of a series of contiguous chemical reactions together constituting a so-called biosynthetic pathway. Each chemical reaction within a biosynthetic pathway is catalyzed by a different plant enzyme, and therefore alkaloid biosynthesis requires that plant enzymes and genes encoding these enzymes, act in concert within the plant cells. Well known examples of plants producing alkaloid compounds, are plants belonging to the Papaveraceae, a plant family constituting approximately 250 species and found mainly in mild and temperate regions of the world. Many alkaloid compounds have been found to have pharmacological effects and have been found useful, as medicinal compounds, as well as recreational drugs or stimulants. Examples of plant alkaloid compounds include the stimulants caffeine and nicotine, the stimulant and local anesthetic cocaine, the anti-malarial drug quinine, the analgesic morphine, the antimicrobials sanguinerine and berberine, the muscle relaxant papaverine and the cough suppressant noscapine.

Currently alkaloid compounds may be harvested from natural sources, such as opium poppy. Alternatively these compounds may be prepared synthetically. The existing manufacturing methods for alkaloid compounds however suffer from low yields and/or are expensive. For example, less than 2% of exogenous (R,S)-norlaudanosoline was converted to sanguinarine via a pathway of 10 genes from opium poppy (*Papaver somniferum*) re-assembled in yeast (*Saccharomyces cerevisiae*) (Fossati et al., 2014). An alternative approach to manufacturing plant alkaloid compounds would comprise marshaling a genetically modified host, e.g. a bacterial or yeast fermentation system, to produce alkaloid compounds. Such a biosynthetic system would permit inexpensive production of plant alkaloids in a tightly controlled environment. However due to the unusual complexity of the synthesis of the vast majority of desirable alkaloid compounds, methods for biosynthesis of alkaloid compounds using inexpensive nutrients and a genetically engineered host system to synthesize alkaloids from such nutrients, are not available. These complexities arise in part from the total number of separate chemical reactions included in a biosynthetic alkaloid production system. Inefficiencies in the performance of each reaction, starting from an economically available substrate, effectively are amplified along the chain of contiguous enzymes, thereby substantially compromising the yield of a final desired alkaloid product.

Thus is unclear whether and how existing methodologies may be used to achieve commercial biosynthesis of plant alkaloid compounds and their derivatives. There exists therefore in the art a need for improved methods for the biosynthesis of alkaloid compounds.

SUMMARY OF THE DISCLOSURE

The following paragraphs are intended to introduce the reader to the more detailed description that follows and not to define or limit the claimed subject matter of the present disclosure.

The present disclosure relates to improved polynucleotide sequences useful in the synthesis of alkaloid compounds, as well as to methods of preparing such improved polynucleotide sequences.

Accordingly, the present disclosure provides, in at least one aspect, at least one embodiment of a method of preparing an improved polynucleotide sequence for the biosynthesis of an alkaloid compound, the method comprising:
  (a) providing a plurality of plant species capable of synthesizing an alkaloid compound;
  (b) preparing a polynucleotide library from a polynucleotide fraction obtained from each of the plant species, each polynucleotide library comprising a pool of polynucleotides;
  (c) determining the nucleic acid sequences of the polynucleotides in each of the pools of polynucleotides;
  (d) identifying a plurality of candidate polynucleotides from the pools of polynucleotides by comparing the nucleic acid sequence of a polynucleotide known to be involved in the synthesis of an alkaloid compound with the nucleic acid sequences of the polynucleotides in the pools, and identifying a plurality of candidate polynucleotides, each of which comprises a nucleic acid sequence substantially identical to the nucleic acid sequence of the polynucleotide known to be involved in the synthesis of alkaloid compounds;
  (e) evaluating synthesis of an alkaloid compound using an expression system that permits the quantitative measurement of the alkaloid compound synthesized using the candidate polynucleotides; and
  (f) selecting from the candidate polynucleotides a polynucleotide providing an improved amount of the alkaloid compound in the expression system.

In a preferred embodiment of the present disclosure, the polynucleotide library is a cDNA polynucleotide library prepared from an alkaloid synthesizing tissue, and accordingly the candidate polynucleotides are cDNA polynucleotides.

In further preferred embodiments, the selected polynucleotide encodes a substantially specific alkaloid biosynthetic enzyme.

In a further aspect, the present disclosure relates to methods for the production of an alkaloid compound in a cell. Accordingly, the present disclosure further includes a method of producing an alkaloid compound in a host cell, the method comprising:

(a) providing a first chimeric nucleic acid sequence comprising as operably linked components:
 (i) a first polynucleotide obtainable from a first plant capable of producing an alkaloid compound encoding a first enzyme capable of catalyzing a chemical reaction that converts a first alkaloid compound into a second alkaloid compound; and
 (ii) one or more polynucleotides capable of controlling expression in a cell;

(b) providing a second chimeric nucleic acid sequence comprising as operably linked components:
 (i) a second polynucleotide obtainable from a second plant capable of producing an alkaloid compound encoding a second enzyme capable of catalyzing a chemical reaction that converts the second alkaloid compound into a third alkaloid compound; and
 (ii) one or more polynucleotides capable of controlling expression in a cell;

(c) introducing the first and second chimeric nucleic acid sequence into the host cell; and (d) growing the cell to produce the first and second enzyme and the second and third alkaloid compound; and wherein the first and second polynucleotide are non-homologous and wherein the third alkaloid compound is produced in the cell at a level in excess of the level of alkaloid produced when a homologous first and second polynucleotide are used.

The present disclosure further provides in at least one aspect at least one embodiment of making an alkaloid compound, comprising:

(a) providing a first alkaloid compound;
(b) contacting the alkaloid compound with an O-methyltransferase and/or an N-methyltransferase under reaction conditions that permit methylation of the alkaloid compound to form a second alkaloid compound;

wherein the first alkaloid compound has the chemical formula:

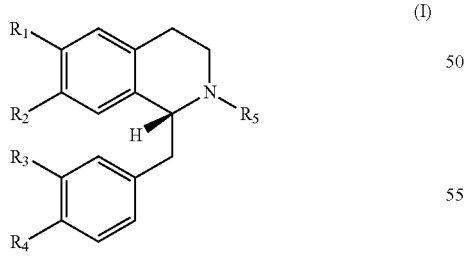

(I)

wherein $R_1$, $R_2$, $R_3$ and $R_4$ each independently or simultaneously represent a hydroxyl group or a methoxy group, with the proviso that $R_1$, $R_2$, $R_3$ and $R_4$ do not each simultaneously represent a methoxy group, and wherein $R_5$ represents a hydrogen atom or a methyl group;

and wherein the second alkaloid compound has the chemical formula:

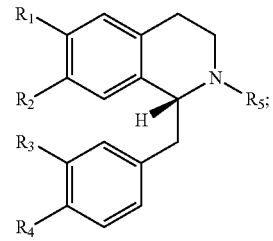

(II)

and wherein $R_1$, $R_2$, $R_3$ and $R_4$ each independently or simultaneously represent a hydroxyl group or a methoxy group, with the proviso that at least one of $R_1$, $R_2$, $R_3$ and $R_4$ represents a methoxy group, and wherein $R_5$ represents a hydrogen atom or a methyl group.

In preferred embodiments the O-methyltransferase is a methyltransferase obtainable or obtained from *Glaucum flavium*.

The present disclosure further includes, in at least one aspect, at least one embodiment of a method of making an alkaloid compound, comprising:

(a) providing a first alkaloid compound;
(b) contacting the alkaloid compound with an O-methyltransferase under reaction conditions that permit methylation of the alkaloid compound to form a second alkaloid compound;

wherein the first alkaloid compound has the chemical formula:

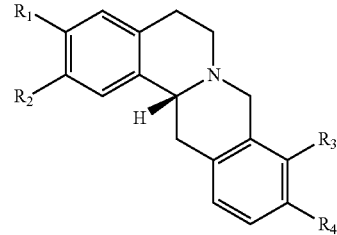

(III)

wherein $R_1$, $R_2$, $R_3$ and $R_4$ each independently or simultaneously represent a hydroxyl group or a methoxy group, with the proviso that $R_1$, $R_2$, $R_3$ and $R_4$ do not each simultaneously represent a methoxy group;

and wherein the second alkaloid compound has the chemical formula:

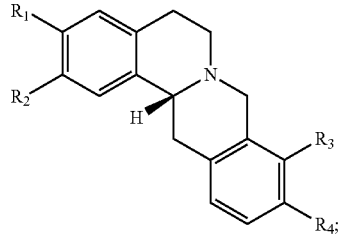

(IV)

and wherein $R_1$, $R_2$, $R_3$ and $R_4$ each independently or simultaneously represent a hydroxyl group or a methoxy group, with the proviso that at least one of $R_1$, $R_2$, $R_3$ and $R_4$ represents a methoxy group.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description

BRIEF DESCRIPTION OF THE DRAWINGS AND TABLES

The disclosure is in the hereinafter provided paragraphs described in relation to its Figures and Tables. The Figures and Tables provided herein are provided for illustration purposes and are not intended to limit the present disclosure.

FIG. 1 depicts N-methylation reactions catalyzed by CNMT, PavNMT and TNMT, and the proposed NMT-catalyzed conversion of (S)-corytuberine to (+)-magnoflorine. CNMT catalyzes the formation of (S)—N-methylcoclaurine from the 1-benzylisoquinoline (S)-coclaurine, PavNMT converts (S)-pavine to (S)—N-methylpavine, and TNMT N-methylates several different protoberberine alkaloids such as (S)-stylopine.

Figure 2:
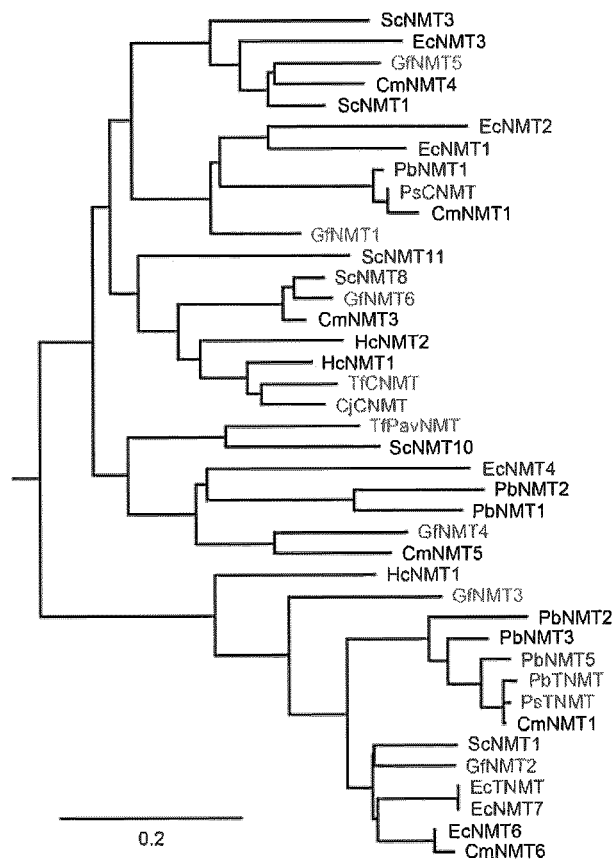

FIG. 2 depicts a phylogenetic analysis of N-methyltransferase (NMT) candidates in the 454 and Illumina GA databases of 20 BIA-producing plant species listed in TABLES 2-4. A total of 33 full-length cDNA sequences NMTs were found. Several functionally characterized NMTs are indicated in red. Sequences from *Glaucium flavum* are shown in green. Abbreviations and accession numbers: PsCNMT, *Papaver somniferum* coclaurine N-methyltransferase (AAP45316); TfCNMT, *Thalictrum flavum* coclaurine N-methyltransferase (AY610508); CjCNMT *Coptis japonica* coclaurine N-methyltransferase (BAB71802); TfPavNMT, *Thalictrum flavum* pavine N-methyltransferase (EU883010); EcTNMT, *Eschscholzia californica* tetrahydroprotoberberine N-methyltransferase (EU882977); PbTNMT, *Papaver bracteatum* tetrahydroprotoberberine N-methyltransferase (EU882994); PsTNMT, *Papaver somniferum* tetrahydroprotoberberine N-methyltransferase (DQ028579); Cm, *Chelidonium majus*; Gf, *Glaucium flavum*; Hc, *Hydrastis canadensis*; Sc, *Sanguinaria canadensis*.

Figure 3:
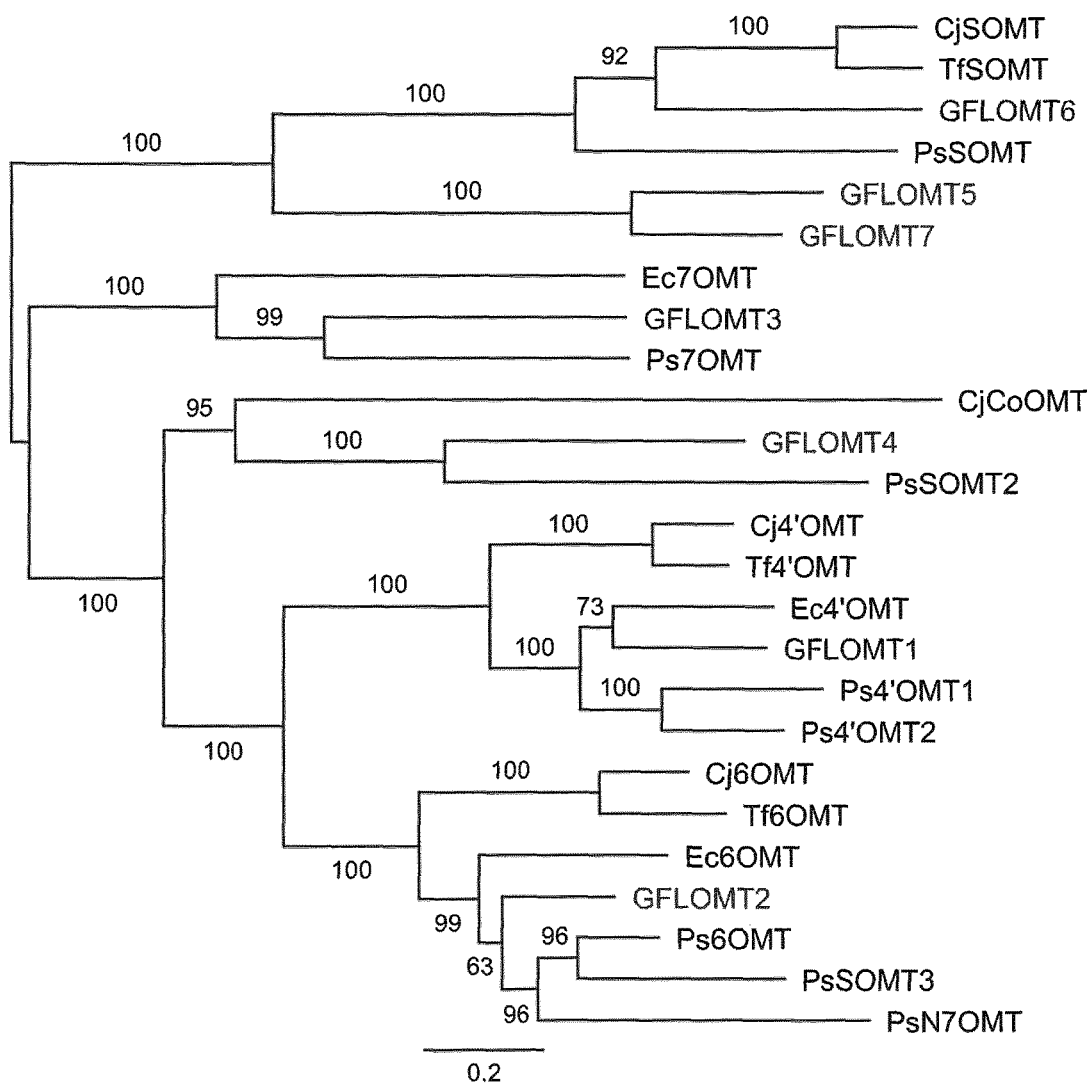

FIG. 3 depicts a phylogenetic analysis of O-methyltransferase (OMT) candidate sequences. Candidates in the 454 and Illumina GA databases of 20 BIA-producing plant species listed in TABLES 2-4. A total of 25 cDNA OMTs were identified. Sequences of *Glaucium flavum* are shown in red. Abbreviations: GFLOMT1-GFLOMT7: *Glaucum flavium* OMT1 to OMT7; PsSOMT-PsSOMT3: *Papaver somniferum* OMT to OMT 3; Ps4'OMT1-PS4'OMT2: *Papaver somniferum* 4'OMT1 to 4'OMT2; Ps6OMT-Ps7OMT: *Papaver somniferum* 6OMT to 7OMT; PsN7OMT: *Papaver somniferum* N7OMT; Ec6OMT-Ec7OMT: *Eschscholzia californica* 6OMT to 7OMT; Ec4'OMT: *Eschscholzia californica* Ec4'OMT; CjSOMT: *Coptis japonica* OMT; JcCoOMT: *Coptis japonica* CoOMT; Cj 4'OMT: *Coptis japonica* 4'OMT; Cj6OMT: *Coptis japonica* 6OMT; Tf4'OMT: *Thalictrum flavum* 4'OMT; and Tf6OMT: *Thalictrum flavum* 6OMT.

Figure 4:
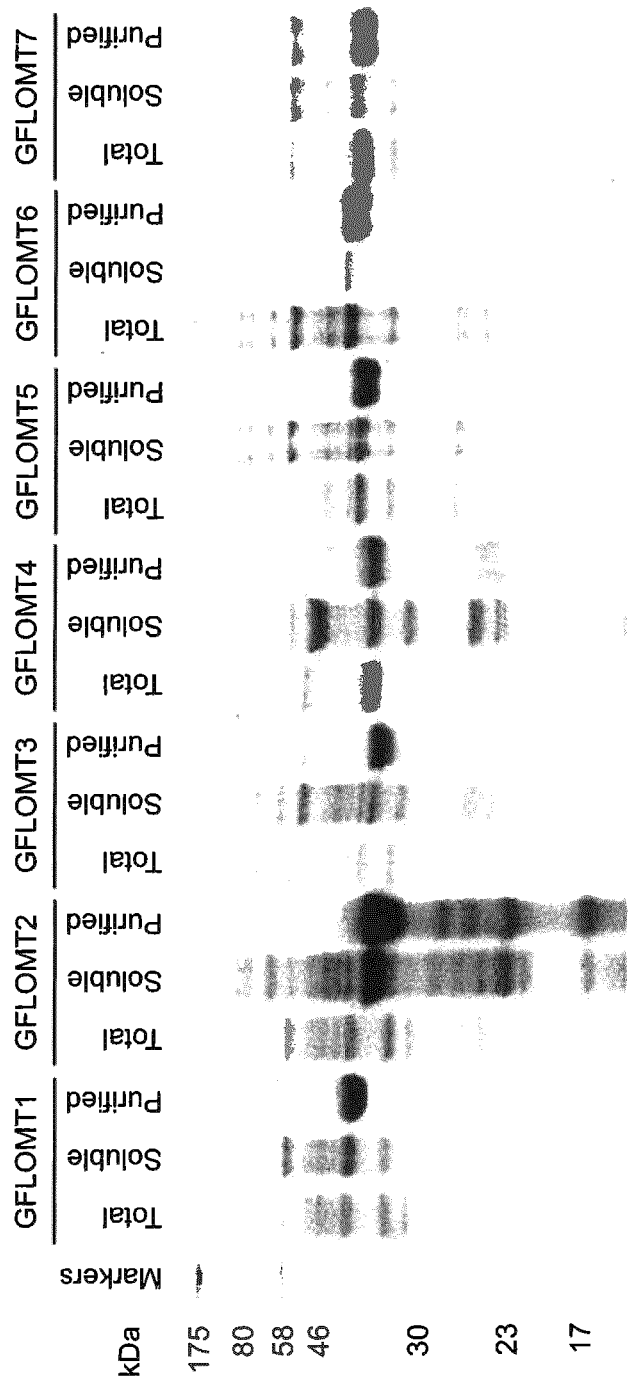

FIG. 4 shows a coomassie blue stained gel following gel electrophoresis of *E. coli* protein extracts expressing various *Glaucium flavum* O-methyl transferases (GFLOMT1-GFLOMT7). Shown for each GFLOMT1 to GFLOMT7 are total extract, soluble protein and purified OMT.

Figure 5:
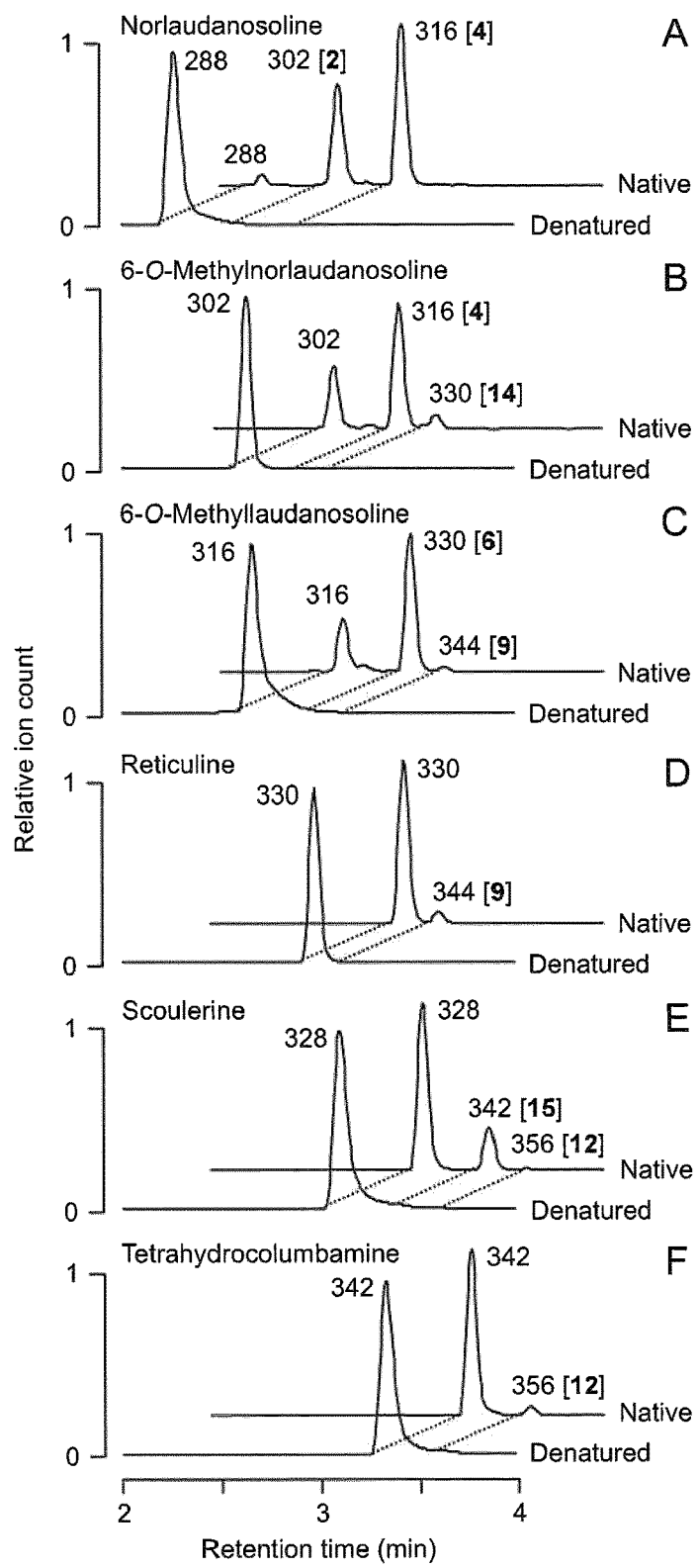

FIG. 5 depicts the results obtained from positive-mode electrospray ionization (ESI[+]) LC-MS/MS for reaction product characterization, including collision-induced dissociation (CID) fragmentation analysis upon incubation of GFLOMT1 with Norlaudanosoline (FIG. 5A), 6-O-Methyl-norlaudanosoline (FIG. 5B), 6-O-Methyllaudanosoline (FIG. 5C), Reticuline (FIG. 5D), Scoulerine (FIG. 5E) and Tetrahydrocolumbamine (FIG. 5F)

Figure 6:
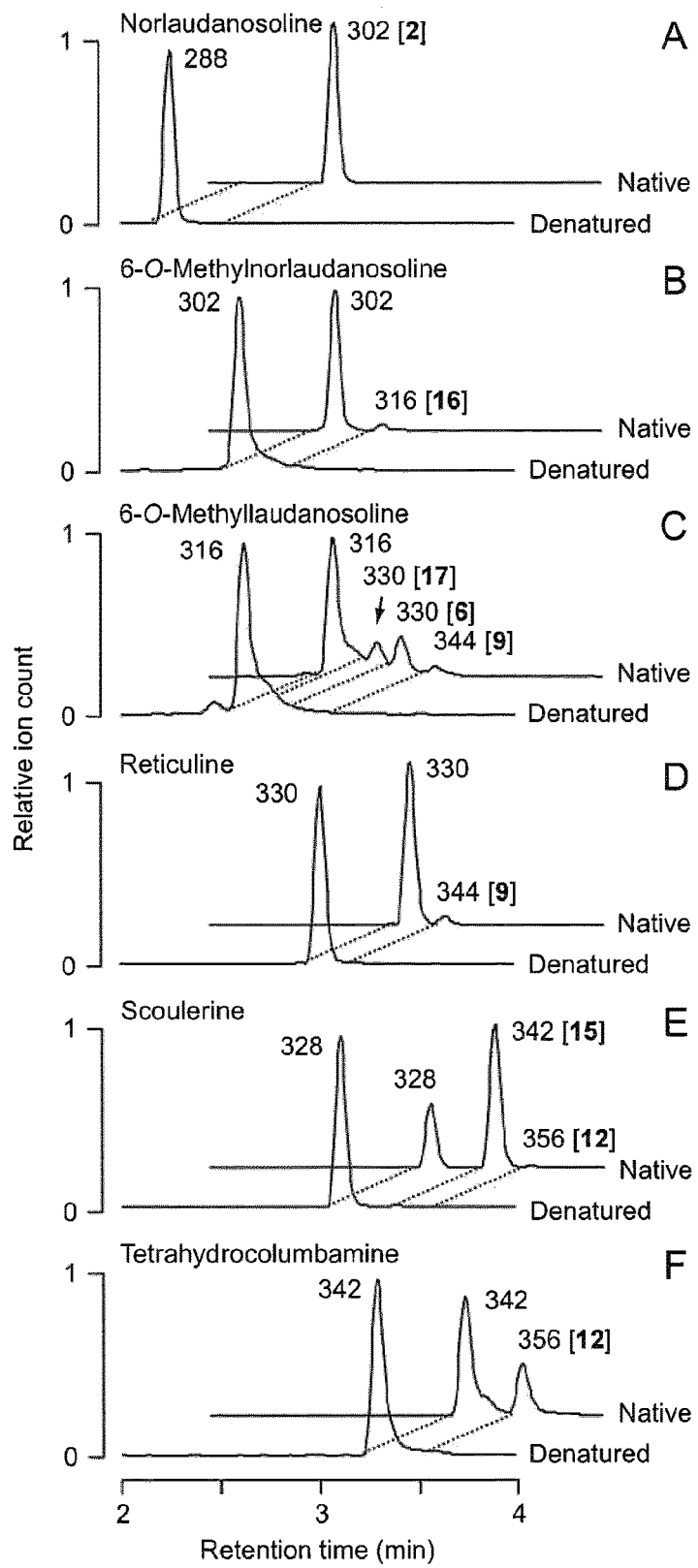

FIG. 6 depicts the results obtained from positive-mode electrospray ionization (ESI[+]) LC-MS/MS for reaction product characterization, including collision-induced dissociation (CID) fragmentation analysis using GFLOMT2 upon incubation of GFLOMT2 with Norlaudanosoline (FIG. 6A), 6-O-Methylnorlaudanosoline (FIG. 6B), 6-O-Methyllaudanosoline (FIG. 6C), Reticuline (FIG. 6D), Scoulerine (FIG. 6E) and Tetrahydrocolumbamine (FIG. 6F)

Figure 7:
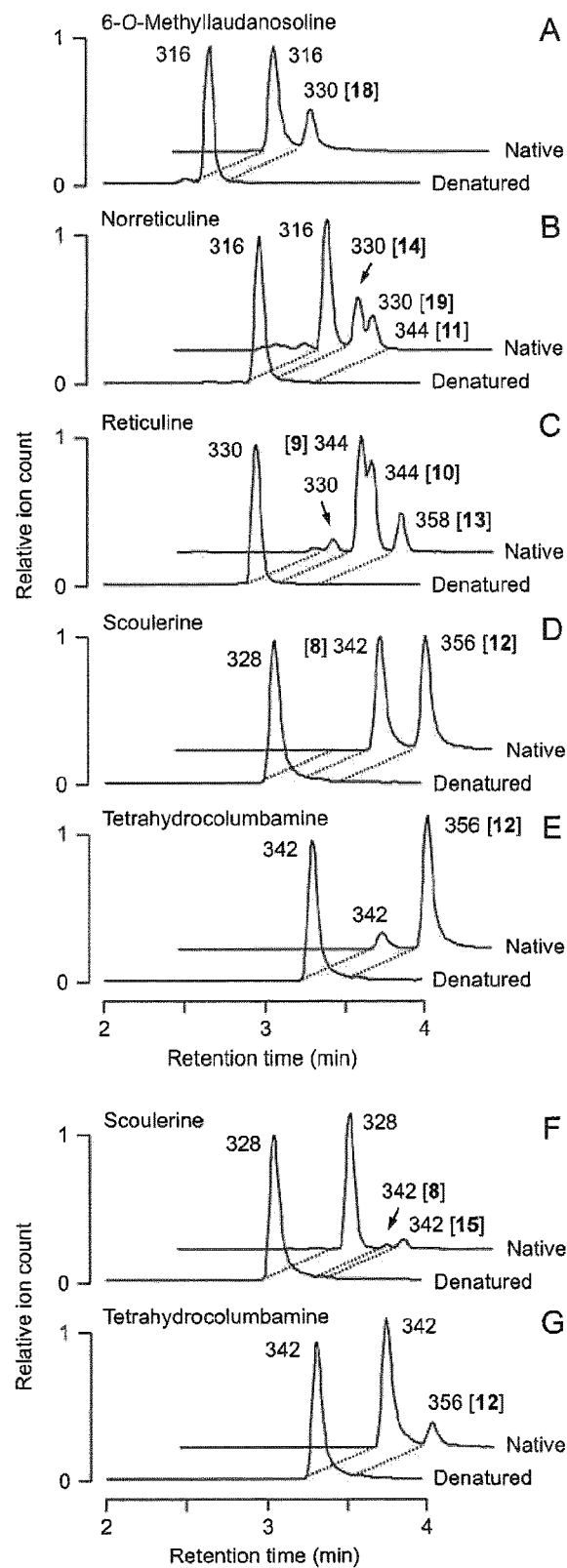

FIG. 7 depicts the results obtained from positive-mode electrospray ionization (ESI[+]) LC-MS/MS for reaction product characterization, including collision-induced dissociation (CID) fragmentation analysis upon incubation of GFLOMT6 with, 6-O-Methyllaudanosoline (FIG. 7A), Norreticuline (FIG. 7B) Reticuline (FIG. 7C), Scoulerine (FIG. 7D) and Tetrahydrocolumbamine (FIG. 7E) and incubation of GFLOMT7 with Scoulerine (FIG. 7F) and Tetrahydrocolumbamine (FIG. 7G).

Figure 8:
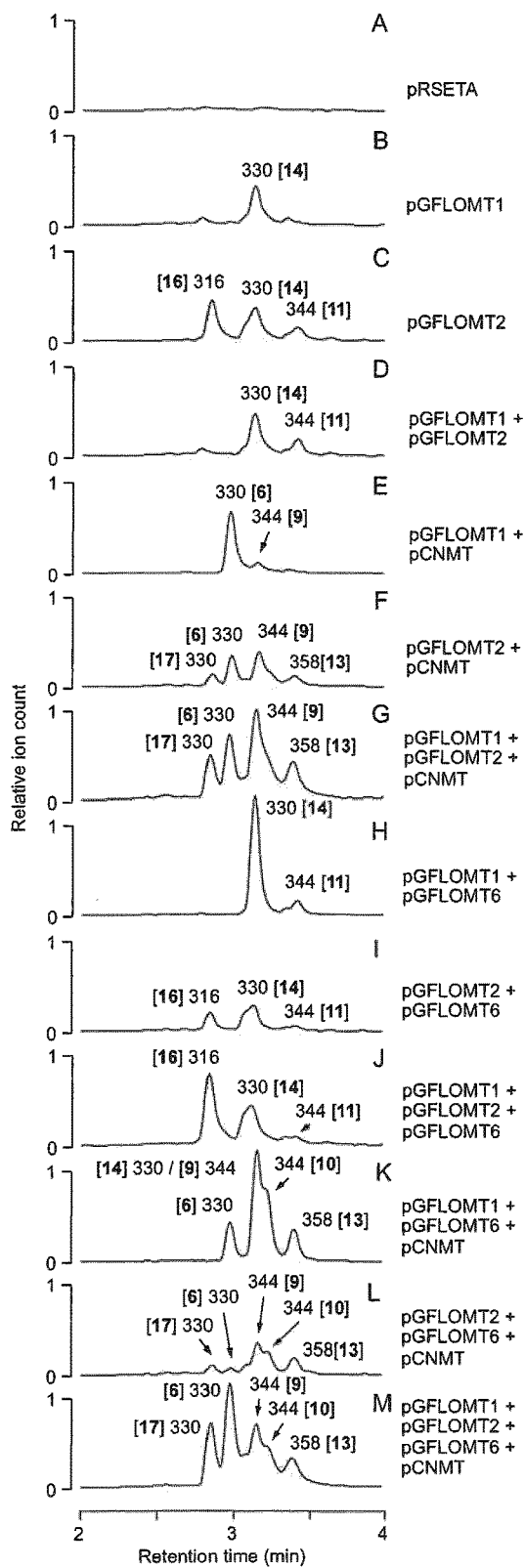

FIG. 8 depicts the results obtained from positive-mode electrospray ionization (ESI[+]) LC-MS/MS for reaction product characterization, including collision-induced dissociation (CID) fragmentation analysis using (R,S)-Norlaudanosoline fed to mixed cultures of *E. coli* harboring different combinations and the various permutations of pGFLOMT1, pGFLOMT2, pGFLOMT6, and pCNMT indicated in FIG. 8A-FIG. 8M).

Figure 9:
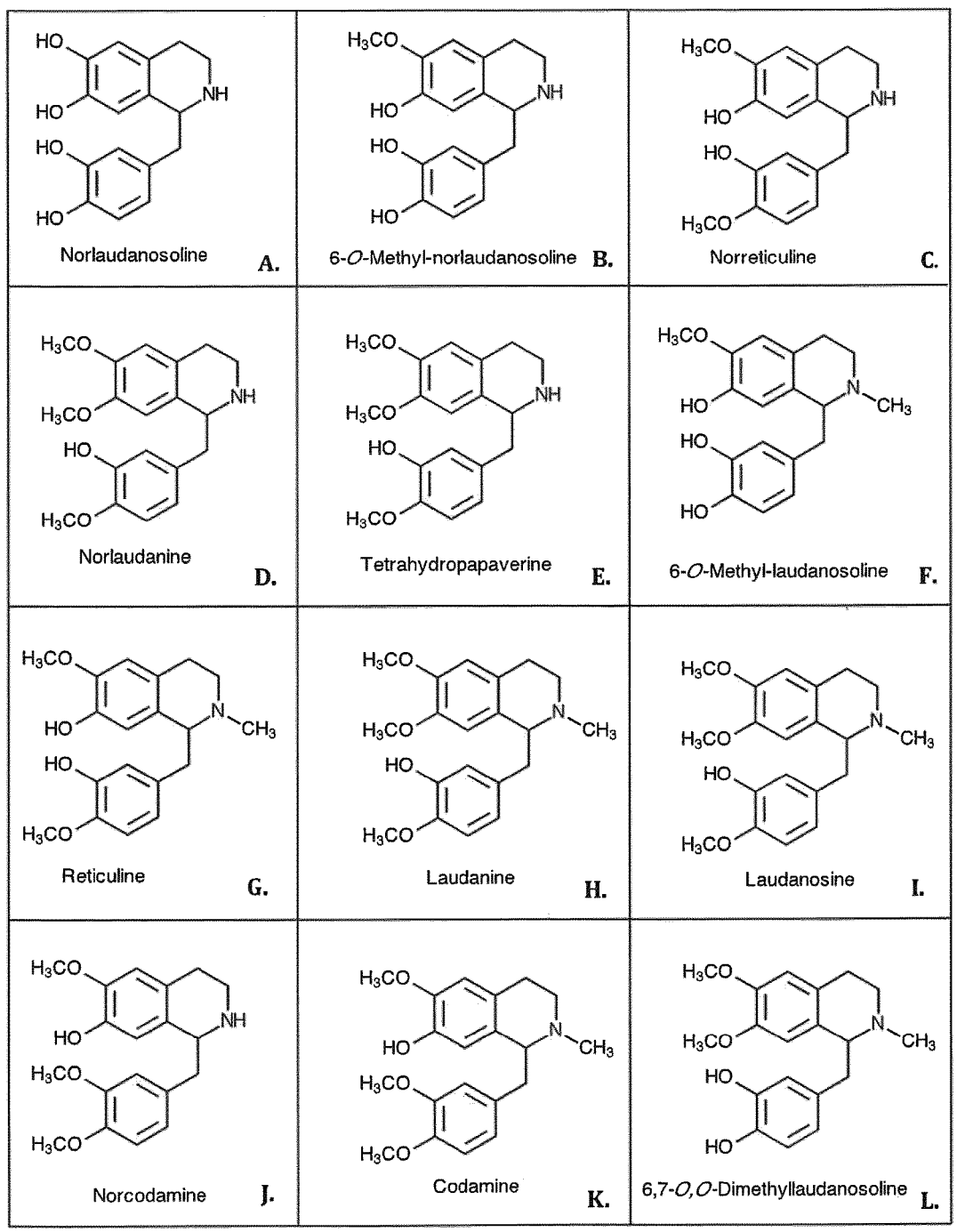

FIG. 9 depicts the chemical structures for certain alkaloid compounds including Norlaudanosoline (FIG. 9A); 6-O-Methyl-norlaudansoline (FIG. 9B); Norreticuline (FIG. 9C); Norlaudanine (FIG. 9D); Tetrahydropapaverine (FIG. 9E); 6-O-Methyl-laudanosoline (FIG. 9F); Reticuline (FIG. 9G); Laudanine (FIG. 9H); Laudanosine (FIG. 9I); Norcodamine (FIG. 9J); Codamine (FIG. 9K) and 6,7-O—O-Dimethyllaudanosoline (FIG. 9L).

Figure 10:
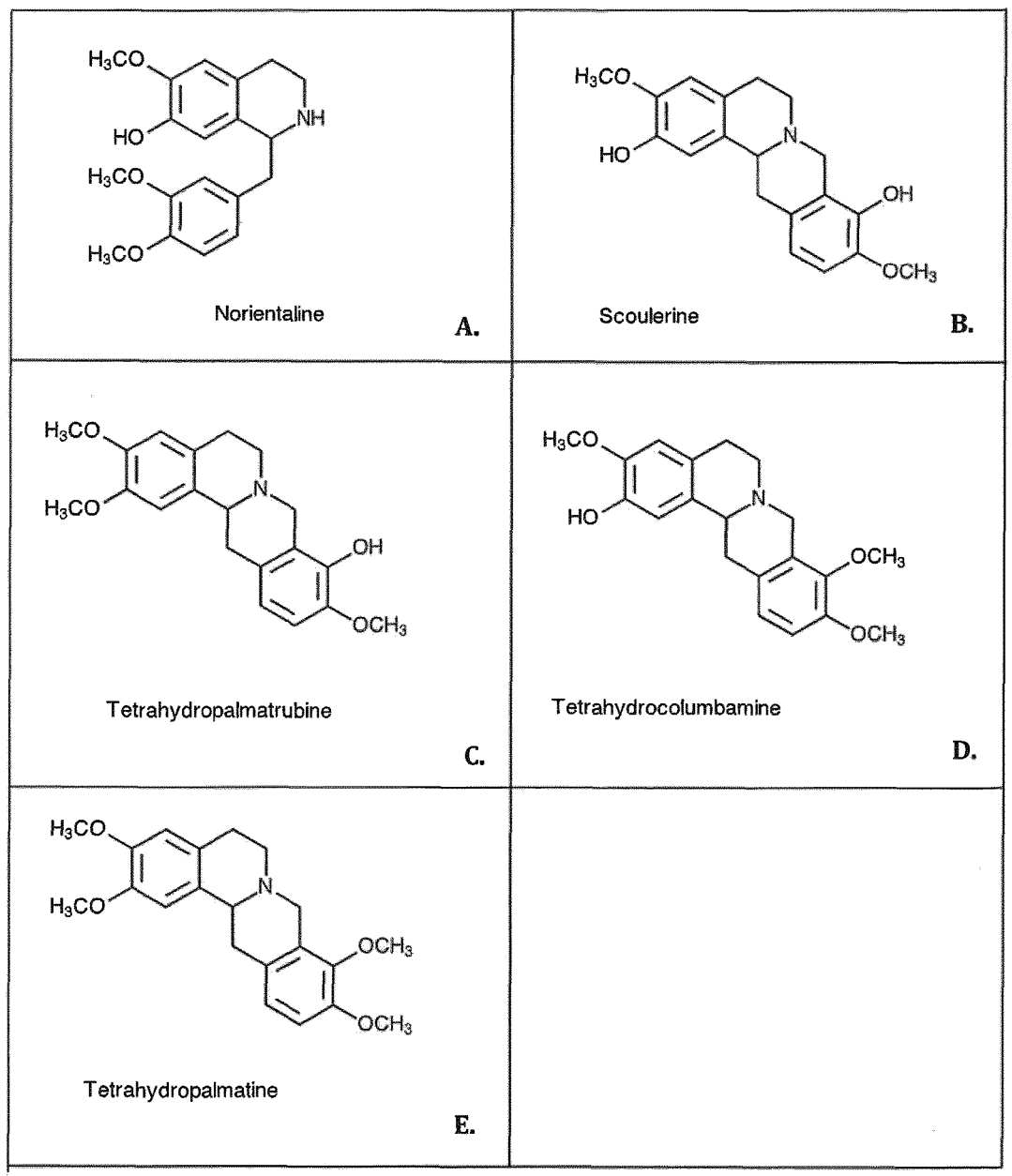

FIG. 10 depicts the chemical structures of certain alkaloid compounds, including Norientaline (FIG. 10A), Scoulerine (FIG. 10B), Tetrahydropalmatrubine (FIG. 10C), Tetrahydrocolumbamine (FIG. 10D) and Tetrahydropalmatine (FIG. 10E).

TABLE 1 tabulates exemplary enzymes, including references to amino acid and polynucleotide SEQ. ID NO's provided herein, and exemplary products and substrates for such enzymes.

TABLE 2 tabulates the denoted information relating to the GS-FLX Titanium (Roche) sequencing of 20 alkaloid producing plant species provided in the column labeled "Plant".

TABLE 3 tabulates the denoted information relating to the GA/HiSeq (illumina) sequencing of 20 alkaloid producing plant species provided in the column labeled "Plant".

TABLE 4 tabulates comparative information relating to the GS-FLX Titanium sequencing and GA/HiSeq sequencing of 20 alkaloid producing plant species provided in the column labeled "Plant".

TABLE 5 tabulates the substrate specificity for the denoted substrates of seven *Glaucium flavum* O-methyl transferases (GFLOMT1-GFLOMT7)

TABLE 6 tabulates chromatographic and mass spectral data for authentic benzylisoquinoline alkaloid standards.

TABLE 7 tabulates chromatographic and mass spectral data for the reaction products of recombinant GFLOMTs assayed with various substrates. ESI[+]-CID fragments in red and green are diagnostic for the number of O-methyl and/or N-methyl groups on the isoquinoline and benzyl moieties, respectively, of each reaction product. Compound names in blue were inferred from the ESI[+]-CID data. Numbers in square brackets identify compounds on chromatograms.

DETAILED DESCRIPTION OF THE DISCLOSURE

As hereinbefore mentioned, the current disclosure relates to polynucleotides useful in the synthesis of alkaloid compounds, such as benzyl isoquinoline alkaloids. The herein provided methods represent an efficient means for identifying novel improved polynucleotides useful in the synthesis of alkaloid compounds. These methods permit rapid identification and testing of candidate polynucleotide sequences for their utility in alkaloid synthesis. The methods of the present disclosure result in a significant improvement in the efficiency of individual chemical reactions in an alkaloid biosynthesis pathway. The techniques in particular improve substrate specificity of one or more enzymes in a biosynthetic pathway, thereby improving the efficiency with which a desired alkaloid product can be synthesized. The methods of the present disclosure do not rely on the prediction of enzyme function based on sequence information and/or structural enzyme models. The present disclosure also relates to methods of making alkaloid compounds. The methods for synthesis of alkaloids provided herein do not rely on chemical synthesis and may be conducted on a commercial scale.

Accordingly, the present disclosure provides in at least one aspect at least one embodiment a method of preparing an improved polynucleotide sequence for the biosynthesis of an alkaloid compound, the method comprising:
  (a) providing a plurality of plant species capable of synthesizing an alkaloid compound;
  (b) preparing a polynucleotide library from a polynucleotide fraction obtained from each of the plant species, each polynucleotide library comprising a pool of polynucleotides;
  (c) determining the nucleic acid sequences of the polynucleotides in each of the pools of polynucleotides;
  (d) identifying a plurality of candidate polynucleotides from the pools of polynucleotides by comparing the nucleic acid sequence of a polynucleotide known to be involved in the synthesis of an alkaloid compound with the nucleic acid sequences of the polynucleotides in the pools, and identifying a plurality of candidate polynucleotides, each of which comprises a nucleic acid sequence substantially identical to the nucleic acid sequence of the polynucleotide known to be involved in the synthesis of alkaloid compounds;
  (e) evaluating synthesis of an alkaloid compound using an expression system that permits the quantitative measurement of the alkaloid compound synthesized using the candidate polynucleotides; and
  (f) selecting from the candidate polynucleotides a polynucleotide providing an improved amount of the alkaloid compound in the expression system.

Definitions

The terms "alkaloid" or "alkaloid compound", as may be used interchangeably herein, refers to naturally occurring chemical compounds containing basic nitrogen atoms, and derivatives and analogues thereof, including, but not limited to compounds belonging to the pyridine group (for example, piperine and nicotine); the pyrrolidine group (for example, hygrine, cuscohygrine, nicotine); the tropane group (for example, atropine, and cocaine); the quinoline group (for example, quinine, quinidine, dihydroquinine, dihydroquinidine, strychnine); the isoquinoline group (for example, opium alkaloids (papaverine, narcotine, narceine); the phenanthrene alkaloid group (for example, the opium alkaloids (morphine, codeine, thebaine)); the phenethyl amine group (for example, mescaline, ephedrine, dopamine); the indole group which includes tryptamines (for example, serotonin), ergolines (for example, ergine, ergotamine, lysergic acid, LSD), beta-carbolines (for example, harmine, harmaline, tetrahydroharmine), yohimbans (for example, reserpine, yohimbine), vinca alkaloids (for example, vinblastine, vincristine), mitragyna speciosa alkaloids (for example, mitragynine, 7-hydroxymitragynine), tabernanthe iboga alkaloids (for example, ibogaine, voacangine, coronaridine, 18-methoxycoronaridine), strychnos nuxvomica alkaloids (for example, strychnine, brucine); the purine group (for example, xanthines: caffeine, theobromine, theophylline); the terpenoid group which include aconite alkaloids (aconitine), steroid alkaloids (containing a steroid skeleton in a nitrogen containing structure, for example, solanum (for example, potato and tomato) alkaloids (solanidine, solanine, chaconine), veratrum alkaloids (veratramine, cyclopamine, cycloposine, jervine, muldamine), newt alkaloids (samandarin), and others (for example, conessine); quaternary ammonium compound group (for example, muscarine, choline, neurine); and miscellaneous alkaloids such as, for example, capsaicin, cynarin, phytolaccine, and phytolacco toxin.

The term Norlaudanosoline as used herein refers to a chemical compound having the chemical structure depicted in FIG. 9A.

The term 6-O-Methyl-norlaudansoline as used herein refers to a chemical compound having the chemical structure depicted in FIG. 9B.

The term Norreticuline as used herein refers to a chemical compound having the chemical structure depicted in FIG. 9C.

The term Norlaudanine as used herein refers to a chemical compound having the chemical structure depicted in FIG. 9D.

The term Tetrahydropapaverine as used herein refers to a chemical compound having the chemical structure depicted in FIG. 9E.

The term 6-O-Methyl-laudanosoline as used herein refers to a chemical compound having the chemical structure depicted in FIG. 9F.

The term Reticuline as used herein refers to a chemical compound having the chemical structure depicted in FIG. 9G.

The term Laudanine as used herein refers to a chemical compound having the chemical structure depicted in FIG. 9H.

The term Laudanosine as used herein refers to a chemical compound having the chemical structure depicted in FIG. 9I.

The term Norcodamine as used herein refers to a chemical compound having the chemical structure depicted in FIG. 9J.

The term Codamine as used herein refers to a chemical compound having the chemical structure depicted in FIG. 9K.

The term 6,7-O—O-Dimethyllaudanosoline as used herein refers to a chemical compound having the chemical structure depicted in FIG. 9L.

The term Norientaline as used herein refers to a chemical compound having the chemical structure depicted in FIG. 10A.

The term Scoulerine as used herein refers to a chemical compound having the chemical structure depicted in FIG. 10B.

The term Tetrahydropalmatrubine as used herein refers to a chemical compound having the chemical structure depicted in FIG. 10C.

The term Tetrahydrocolumbamine as used herein refers to a chemical compound having the chemical structure depicted in FIG. 10D.

The term Tetrahydropalmatine as used herein refers to a chemical compound having the chemical structure depicted in FIG. 10E.

The term "cDNA" as used herein refers to all polynucleotides that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

The term "homologous" as used herein in reference to polynucleotides and polynucleotide sequences is intended to mean obtainable from the same biological species, i.e. a first and second polynucleotide sequence are homologous when they are obtainable from the same biological species, and conversely, a first and second polynucleotide sequence are non-homologous when they are obtainable or obtained from two different biological species.

The term "in vitro" as used herein refers to the performance of a biochemical reaction outside a living cell, including, for example, in a microwell plate, a tube, a flask, a tank, a reactor and the like, for example a reaction to form an alkaloid compound.

The term "in vivo" as used herein refers to the performance of a biochemical reaction within a living cell, including, for example, a microbial cell, or a plant cell, for example to form an alkaloid compound.

The term "polynucleotide" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The term "percent sequence identity" refers to the degree of identity between any given query sequence and a subject sequence. A subject sequence typically has a length that is from about 80 percent to about 250 percent of the length of the query sequence, e.g., 82, 85, 87, 89, 90, 93, 95, 97, 99, 100, 105, 110, 115, or 120, 130, 140, 150, 160, 170, 180, 190, 200, 210, 220, 230, 240, or 250 percent of the length of the query sequence. A query nucleic acid or amino acid sequences is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) Nucleic Acids Res. 31(13):3497-500. Optimal alignment of sequences for comparison may be conducted by the local homology algorithm of Smith and Waterman (1981) Add. APL. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85: 2444, by computerized implementations of algorithms such as GAP, BESTFIT, BLAST, PASTA, and TFASTA (Wisconsin Genetics Software Package, Genetics Computer Group (GCG), 575 Science Dr., Madison, Wis.) or by inspection. Typically, the default values of 5.00 for gap weight and 0.30 for gap weight length are used. ClustalW calculates the best match between a query and one or more subject sequences, and aligns them so that identities, similarities and differences can be determined Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web. To determine a percent identity for polypeptide or nucleic acid sequences between a query and a subject sequence, the sequences are aligned using Clustal W and the number of identical matches in the alignment is divided by the query length, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity, however in each case less than 100%, compared to a reference polynucleotide sequence using the programs.

The terms "O-methyltransferase", or "OMT", which may be used interchangeably herein, refer to any and all enzymes comprising a sequence of amino acid residues which is (i) substantially identical to the amino acid sequences constituting any OMT polypeptide set forth herein, including, for example, SEQ. ID NO: 1592, SEQ. ID NO: 1593; SEQ. ID NO: 1597; and SEQ. ID NO: 1598, or (ii) encoded by a nucleic acid sequence capable of hybridizing under at least moderately stringent conditions to any nucleic acid sequence encoding any OMT polypeptide set forth herein, but for the use of synonymous codons.

The terms "N-methyltransferase", or "NMT", which may be used interchangeably herein, refer to any and all enzymes comprising a sequence of amino acid residues which is (i) substantially identical to the amino acid sequences constituting any NMT polypeptide set forth herein, including, for example, SEQ. ID NO: 1749, or (ii) encoded by a nucleic acid sequence capable of hybridizing under at least moderately stringent conditions to any nucleic acid sequence encoding any NMT polypeptide set forth herein, but for the use of synonymous codons.

General Implementation

In one embodiment of the present disclosure, there is provided a method of preparing an improved polynucleotide sequence for the biosynthesis of an alkaloid compound. In one aspect, the herein provided method involves providing a plurality of plant species capable of synthesizing an alkaloid compounds. Alkaloid compounds that are particularly preferred in accordance herewith are benzylisoquinoline alkaloids, including L-tyrosine, tyramine, dopamine, 4-hydroxyphenylpyruvate, 4-hydroxyphenylacetaldehyde, (S)—Nocroclaurine, (S)-1-hydroxy-N-methylcanadine, narcotinohemiacetal, noscapine, (S)—N-methylcanadine, (S)-coclaurine, (S)-norreticuline, (S)-tetrahydropapaverine, papaverine, oripavine, thebaine, salutardinol, (S)—N-methylcoclaurine, (S)-canadine, berberine, berbamunine, morphinone, codeinone, salturadine, coryturbine, (S)-3-hydroxy-N-methylcoclaurine, (S)-tetrahydrocolumbamine, (S)-tetrahydropalmatine, morphine, codeine, (R)-reticuline, (S)-reticuline, (S)-scoulerine, (S)-cheilanthifoline, sanguinarine, dihydrosanguinarine, protopine, (S)-cis-N-methylstylopine, (S)-stylopine, 1-benzylisoquinoline, protoberberine, papverubine, aporphine, benzo[c]phenanthridine, phtalideisoquinoline, secoisoquinoline, promorphinan, morphinan, pavine, isopavine and bisbenzylisoquinoline. Plant species that may be used in accordance herewith include, without limitation, plant species belonging to the plant families of Eupteleaceae, Lardizabalaceae, Circaeasteraceae, Menispermaceae, Berberidaceae, Ranunculaceae, and Papaveraceae (including those belonging to the subfamilies of Pteridophylloideae, Papaveroideae and Fumarioideae) and further includes plants belonging to the genus *Argemone*, including *Argemone mexicana* (Mexican Prickly Poppy), plants belonging to the genus *Berberis*, including *Berberis thunbergii* (Japanese Barberry), plants belonging to the genus *Chelidonium*, including *Chelidonium majus* (Greater Celandine), plants belonging to the genus *Cissampelos*, including *Cissampelos mucronata* (Abuta), plants belonging to the genus *Cocculus*, including *Cocculus trilobus* (Korean Moonseed), plants belonging to the genus *Corydalis*, including *Corydalis chelanthifolia* (Ferny Fumewort), plants belonging to the genus *Eschscholzia*, including *Eschscholzia californica* (California Poppy), plants belonging to the genus *Glaucium*, including *Glaucium flavum* (Yellowhorn Poppy), plants belonging to the genus *Hydrastis*, including *Hydrastis canadensis* (Goldenseal), plants belonging to the genus *Jeffersonia*, including *Jeffersonia diphylla* (Rheumatism Root), plants belonging to the genus *Mahonia*, including *Mahonia aquifolium* (Oregon Grape), plants belonging to the genus *Menispermum*, including *Menispermum canadense* (Canadian Moonseed), plants belonging to the genus *Nandina*, including *Nandina domestica* (Sacred Bamboo), plants belonging to the genus *Nigella*, including *Nigella sativa* (Black Cumin), plants belonging to the genus *Papaver*, including *Papaver bracteatum* (Persian Poppy) and *Papver somniferum*, plants belonging to the genus *Sanguinaria*, including *Sanguinaria canadensis* (Bloodroot), plants belonging to the genus *Stylophorum*, including *Stylophorum diphyllum* (Celandine Poppy), plants belonging to the genus *Thalictrum*, including *Thalictrum flavum* (Meadow Rue), plants belonging to the genus *Tinospora*, including *Tinospora cordifolia* (Heartleaf Moonseed) and plants belonging to the genus *Xanthoriza*, including *Xanthoriza simplicissima* (Yellowroot).

In a further aspect, the herein provided method involves the preparation of a polynucleotide library from a plant. Methods to prepare such polynucleotide library may be as desired. In general, methods to prepare a polynucleotide library involve isolation of a polynucleotide fraction (e.g. a DNA fraction or an RNA fraction) from plant cells, fractionating the polynucleotide fraction into a pool of polynucleotide fragments (preferably DNA fragments), cloning the polynucleotide fragments within the pool into a vector, e.g. a plasmid or viral vector, and maintaining the cloned fragments into a host, e.g. a microbial host such as a bacterial host or a yeast cell host. The techniques and methodologies for preparing a polynucleotide library are well known to those in the art and further details may be found in Sambrook J. and Green M., Molecular Cloning: A Laboratory Manual, 2012, Cold Spring Harbor Press. In a preferred embodiment hereof the polynucleotide library is a cDNA library prepared from a plant tissue synthesizing alkaloid compounds. Such tissue may be any plant tissue synthesizing alkaloids, including for example, plant stem tissue, bark tissue, leaf tissue, seed tissue, fruit tissue, flower tissue, root tissue, rhizome tissue or callus tissue, obtained, for example, from the hereinbefore mentioned plants. In preferred embodiments, the following tissues used in accordance herewith are: stem of *Argemone mexicana* (Mexican Prickly Poppy), root of *Berberis thunbergii* (Japanese Barberry), stem of *Chelidonium majus* (Greater Celandine), callus of *Cissampelos mucronata* (Abuta), callus of *Cocculus trilobus* (Korean Moonseed), root of *Corydalis chelanthifolia* (Ferny Fumewort), root of *Eschscholzia californica* (California Poppy), root of *Glaucium flavum* (Yellowhorn Poppy), rhizome of *Hydrastis canadensis* (Goldenseal), root of *Jeffersonia diphylla* (Rheumatism Root), bark of *Mahonia aquifolium* (Oregon Grape), rhizome of *Menispermum canadense* (Canadian Moonseed), root of *Nandina domestica* (Sacred Bamboo), root of *Nigella sativa* (Black Cumin), stem of *Papaver bracteatum* (Persian Poppy), rhizome of *Sanguinaria canadensis* (Bloodroot), stem of *Stylophorum diphyllum* (Celandine Poppy), root of *Thalictrum flavum* (Meadow Rue), callus of *Tinospora cordifolia* (Heartleaf Moonseed) or root of *Xanthoriza simplicissima* (Yellowroot).

In a further aspect, the herein provided methods involve the determination of the nucleic acid sequence of the polynucleotide fragments in the pools of polynucleotides. Methods to determine the sequences of polynucleotides may be as desired and are well known to the art in include for example Sanger sequencing, GS-FLX Titanium (Roche) sequencing and GA/HiSeq sequencing (Illumina). The latter two are particularly desirable as they provide for high throughput.

In a further aspect, the herein provided methods involve the identification and isolation of candidate polynucleotides from the pools of sequenced polynucleotides. In accordance herewith, this is achieved by comparing a polynucleotide sequence which is known to be involved in the synthesis of alkaloid compounds, i.e. a query sequence, to the sequences of the polynucleotides in the polynucleotide sequences present in the pools, and determining which sequences among the pools of sequenced polynucleotide sequences are substantially identical to the query sequence. The approach to determining substantial identity may vary, but generally involves determining the percentage identity between the query polynucleotide sequence and the polynucleotide sequences in the pools using in general the methodologies hereinbefore described (see: terms and definitions) and identifying such of the sequences that are substantially identical to the sequence of the query polynucleotide. In an alternate approach, substantial identity may also be established by deriving the polypeptide sequence from the polynucleotide sequence (using the known rules for codon use) and comparing a query polypeptide sequence with the sequences in the pool. In accordance herewith, the polynucleotide sequences in the pools that show substantial sequence identity are candidate polynucleotide sequences, which are subsequently isolated from the pools of polynucleotide sequences. In some cases, part coding sequences may be identified and it may be necessary to identify overlapping polynucleotides in order to identify the full-length polynucleotide sequence. Polynucleotide sequences that may be used as query sequences include any polynucleotide sequences known to be involved in the synthesis of any alkaloid. Examples of enzymes encoding such polynucleotide sequences are provided in TABLE 1 hereto. In accordance herewith, in particularly preferred embodiments, the polynucleotide sequences used in accordance herewith include polynucleotide sequences encoding N-methyltransferases (see: Examples 2 and 3), or O-methyltransferases (see: Examples 4, 5, 6 and 7)

In a further aspect, the present disclosure involves evaluating the production of an alkaloid compound using a system that permits the quantitative measurement of the alkaloid compound synthesized using the candidate polynucleotides. In general, the identified candidate polynucleotide sequences may be cloned into an expression vector and introduced into a host cell, which may be any microbial cell, e.g. a bacterial cell or a yeast cell, plant cell or animal cell. Upon such introduction the production of the alkaloid may be evaluated either in vitro or in vivo. In vitro evaluation may be performed by isolating the enzyme in more or less pure form from the host e.g. by evaluating a cellular fraction (e.g. in the case of yeast, a microsome fraction) obtainable from the host cell comprising the enzyme, incubating the enzyme fraction with its alkaloid substrate and assaying for the alkaloid product. In vivo evaluation may be performed by providing to the host cell a substrate or potential substrate alkaloid to the enzyme encoded by the candidate polynucleotide and evaluating the in vivo production of the product alkaloid. The enzyme conversion rate and/or the substrate specificity for a substrate or potential substrate may be determined qualitatively or quantitatively using enzyme assays. Quantitative determination includes, for example, determining the percentage of substrate converted, or determining key catalytic properties of an enzyme such as the $k_{cat}$ and/or $K_m$ of an enzyme. Methodologies to evaluate the production of an alkaloid compound in a quantitative fashion in accordance herewith will be generally known to those of skill in the art, and include for example liquid chromatography-mass spectrometry (LC/MS) or gas chromatography-mass spectrometry (GC/MS). The production of the alkaloid by different candidate polynucleotides and/or the query polynucleotide may be compared.

In one aspect, in accordance herewith, from the candidate polynucleotides a polynucleotide providing an improved amount of the alkaloid compound in the expression system is selected. In preferred embodiments, the selected polynucleotide is a polynucleotide conveying higher levels of production of the target alkaloid compound than those provided by the query polynucleotide and/or by those observed using the query polynucleotide.

In further embodiments, a polynucleotide encoding an enzyme having narrow substrate specificity is selected. The term "narrow substrate specificity" as used herein refers to an enzyme capable of substantially converting no more than 3, or no more than 2 different alkaloid substrates. The term "substantially converting" as used herein refers to an enzyme capable of converting 90% or more, or 95% or more of that substrate to a single product.

In further embodiments, a polynucleotide encoding a substantially specific alkaloid biosynthetic enzyme is selected. The term "substantially specific alkaloid biosynthetic enzyme" as used herein refers to an enzyme which when presented with an alkaloid substrate under assay conditions is capable of converting 90% or more, or 95% or more of that substrate to an alkaloid product, and when presented with other alkaloid substrates under the same assay conditions is capable of converting no more than 20%, 15%, 10% or 5% of such other alkaloid substrates. Thus, for example, an O-methyltransferase capable of converting 99% of a first benzylisoquinoline when presented therewith, and 10%, 5% and 0%, of a second, third and fourth benzylisoquinoline, respectively, when presented with these compounds, is a substantially specific alkaloid biosynthetic enzyme. Conversely, an O-methyltransferase capable of converting 99% of a first benzylisoquinoline when presented therewith, and 75%, 5% and 0%, of a second, third and fourth benzylisoquinoline, respectively, when presented with these compounds is not a substantially specific alkaloid biosynthetic enzyme.

In additional embodiments, the methods herein provided are conducted in an iterative fashion for the purpose of identifying two or more improved polynucleotide sequences encoding enzymes capable of converting two or more alkaloid compounds in an alkaloid synthesis pathway, for example, 3, 4, 5, 6, 7, 8, 9, 10 or more polynucleotides, each encoding a different enzyme in the same alkaloid biosynthesis pathway. In further embodiments, at least 2, 3, 4, 5, 6, 7, 8, 9, or 10 polynucleotides are selected, each polynucleotide encoding an enzyme that has narrow substrate specificity. In further embodiments, at least 2, 3, 4, 5, 6, 7, 8, 9, or 10 polynucleotides are selected, each polynucleotide encoding a substantially specific alkaloid biosynthetic enzyme. Thus a plurality of improved polynucleotides may be identified and each of these improved polynucleotides may be evaluated in conjunction with one or more other improved polynucleotides. In this manner, the alkaloid synthesis pathway may be improved, and improved levels of an alkaloid compound may be obtained. Levels of alkaloid compound production that may be obtained using the improved polynucleotides of the present disclosure in combination with a recombinant host cell system are typically at least 1.5× in excess of the level of the levels of the alkaloid compound produced in a natural system, and in some embodiments at least 2×, 5×, or at least 10× in excess of the levels of the alkaloid compound produced in a natural system.

The present disclosure further includes novel polynucleotides capable of producing an enzyme involved in the biosynthesis of alkaloid compounds. These polynucleotides include the polynucleotide sequences set forth in SEQ. ID NO: 1-SEQ. ID NO: 870.

In accordance with a further aspect of the present disclosure, included herein are methods for the production of alkaloid compounds in a host cell. Accordingly, the present disclosure further includes a method of producing an alkaloid compound in a host cell, the method comprising:

(a) providing a first chimeric nucleic acid sequence comprising as operably linked components:
   (i) a first polynucleotide obtainable from a first plant capable of producing an alkaloid compound encoding a first enzyme capable of catalyzing a chemical reaction that converts a first alkaloid compound into a second alkaloid compound; and
   (ii) one or more polynucleotides capable of controlling expression in a cell;
(b) providing a second chimeric nucleic acid sequence comprising as operably linked components:
   (i) a second polynucleotide obtainable from a second plant capable of producing an alkaloid compound encoding a second enzyme capable of catalyzing a chemical reaction that converts the second alkaloid compound into a third alkaloid compound; and
   (ii) one or more polynucleotides capable of controlling expression in a cell;
(c) introducing the first and second chimeric nucleic acid sequence into the host cell; and
(d) growing the cell to produce the first and second enzyme and the second and third alkaloid compound; and wherein the first and second polynucleotide are non-homologous and wherein the third alkaloid compound is produced in the cell at a level that is in excess of the level of alkaloid compound produced when a homologous first and second polynucleotide are used.

In preferred embodiments hereof, the alkaloid levels produced using the non-homologous polynucleotides are at least 1.5× in excess of the levels produced using homologous polynucleotides, in more preferred embodiments at least 2×, at least 5× or at least 10× in excess. In further preferred embodiments, the first and second polynucleotide are a polynucleotide encoding any one of the polypeptides set forth in SEQ. ID NO: 871 to SEQ. ID NO: 1749.

In further preferred embodiments hereof, the first and second polynucleotide sequences have been obtained by comparing the production of an alkaloid compound in a cell using a plurality of polynucleotides encoding an enzyme capable of catalyzing a chemical reaction converting a first alkaloid compound into a second alkaloid embodiment, and selecting the polynucleotide providing the highest levels of the second alkaloid compound. In preferred embodiments, such selection is performed by:
   (a) providing a plurality of plant species capable of synthesizing an alkaloid compound;
   (b) preparing a polynucleotide library from each of the plant species, each polynucleotide library comprising a pool of polynucleotides;
   (c) determining the nucleic acid sequences of the polynucleotides in each of the pools of polynucleotides;
   (d) isolating a plurality of candidate polynucleotides from the pools of polynucleotides by comparing the nucleic acid sequence of a polynucleotide known to be involved in the synthesis of an alkaloid compound with the nucleic acid sequences of the polynucleotides in the pools, and identifying a plurality of candidate polynucleotides, each of which comprises a nucleic acid sequence substantially identical to the nucleic acid sequence of the polynucleotide known to be involved in the synthesis of alkaloid compounds;
   (e) evaluating synthesis of an alkaloid compound using an expression system that permits the quantitative measurement of the alkaloid compound synthesized using the candidate polynucleotides; and
   (f) selecting from the candidate polynucleotides a polynucleotide providing an improved amount of the alkaloid compound in the expression system.

Polynucleotides capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further polynucleotide elements capable elements of controlling expression in a host cell include transcriptional terminators, enhancers and the like, all of which may be included in the chimeric polynucleotides of the present disclosure.

In accordance with the present disclosure, the chimeric polynucleotides can be integrated into a recombinant expression vector, which ensures good expression in a host cell. Accordingly, the present disclosure includes a recombinant expression vector comprising in the 5' to 3' direction of transcription as operably linked components:
   (i) a first polynucleotide capable of controlling expression in a host cell;
   (ii) a first polynucleotide obtainable from a first plant capable of producing an alkaloid compound encoding a first enzyme capable of catalyzing a chemical reaction that converts a first alkaloid compound into a second alkaloid compound;
   (iii) a second polynucleotide capable of controlling expression in a host cell; and
   (iv) a second polynucleotide obtainable from a second plant capable of producing an alkaloid compound encoding a second enzyme capable of catalyzing a chemical reaction that converts the second alkaloid compound into a third alkaloid compound.

wherein the expression vector is suitable for expression in a host cell. The term "suitable for expression in a host cell" means that the recombinant expression vector comprises the chimeric polynucleotide of the present disclosure linked to genetic elements required to achieve expression in a host cell. Genetic elements that may be included in the expression vector in this regard include a transcriptional termination region, one or more polynucleotides encoding marker genes, one or more origins of replication and the like. In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

One host cell that particularly conveniently may be used is *Escherichia coli*. The preparation of the *E. coli* vectors may be accomplished using commonly known techniques such as restriction digestion, ligation, gelectrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook J. and Green M., Molecular Cloning: A Laboratory Manual, 2012, Cold Spring Harbor Press.

Methods of Using O-Methyltransferases

As hereinbefore mentioned, in certain embodiments, O-methyltransferases are identified. Such O-methyltransferases include the following O-methyltransferases from *Glaucium flavum*, and further include GFLOMT1 (SEQ. ID NO: 1592), GFLOMT2 (SEQ. ID NO: 1593), GFLOMT6 (SEQ. ID NO: 1597) and GFLOMT7 (SEQ. ID NO: 1598). In accordance herewith the O-methyltransferases may be used to methylate a first alkaloid compound and form a second alkaloid compound.

Accordingly, the present disclosure further includes in at least one aspect at least one embodiment of a method of making an alkaloid compound, comprising:

(a) providing a first alkaloid compound;

(b) contacting the alkaloid compound with an O-methyltransferase and/or and N-methyltransferase under reaction conditions that permit methylation of the alkaloid compound to form a second alkaloid compound;

wherein the first alkaloid compound has the chemical formula:

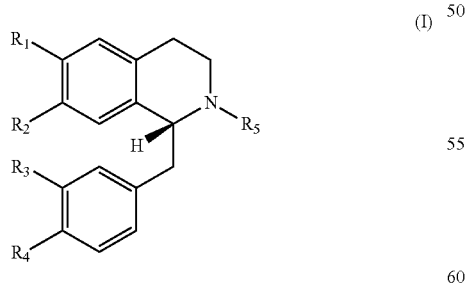

(I)

wherein $R_1$, $R_2$, $R_3$ and $R_4$ each independently or simultaneously represent a hydroxyl group or a methoxy group, with the proviso that $R_1$, $R_2$, $R_3$ and $R_4$ do not each simultaneously represent a methoxy group, and wherein $R_5$ represents a hydrogen atom or a methyl group; and wherein the second alkaloid compound has the chemical formula:

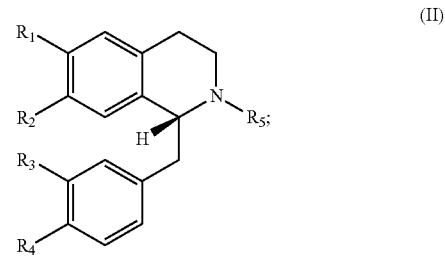

(II)

and wherein $R_1$, $R_2$, $R_3$ and $R_4$ each independently or simultaneously represent a hydroxyl group or a methoxy group, with the proviso that at least one of $R_1$, $R_2$, $R_3$ and $R_4$ represents a methoxy group, and wherein $R_5$ represents a hydrogen atom or a methyl group.

Referring to FIG. 9, in certain embodiments, the first alkaloid compound is a compound selected from the group consisting of Norlaudanosoline, 6-O-Methyl-norlaudanosline, Norreticuline, Norlaudanine, 6-O-Methyl-laudanosline, Reticuline, Norreticuline, Laudanine, Laudanosine, Tetrahydro-papaverine, Codamine and Norcodamine.

Referring to FIG. 9 and FIG. 10, in certain embodiments, the second alkaloid compound is an compound selected from the group consisting of 6-O-Methyl-norlaudanosline, Norreticuline, Norlaudanine, 6-O-Methyl-laudanosline, Reticuline, Norreticuline, Laudanine, Laudanosine, Tetrahydropapaverine, Codamine, 6,7-O,O-Dimethyllaudanosoline, Norcodamine and Norientaline or mixtures thereof.

The present disclosure further includes, in at least one aspect at least one embodiment of a method of making an alkaloid compound, comprising:

(a) providing a first alkaloid compound;

(b) contacting the alkaloid compound with an O-methyltransferase under reaction conditions that permit methylation of the alkaloid compound to form a second alkaloid compound;

wherein the first alkaloid compound has the chemical formula:

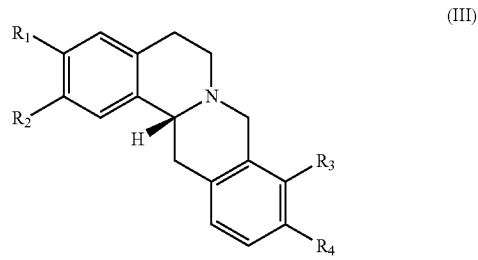

(III)

wherein $R_1$, $R_2$, $R_3$ and $R_4$ each independently or simultaneously represent a hydroxyl group or a methoxy group, with the proviso that $R_1$, $R_2$, $R_3$ and $R_4$ do not each simultaneously represent a methoxy group;

and wherein the second alkaloid compound has the chemical formula:

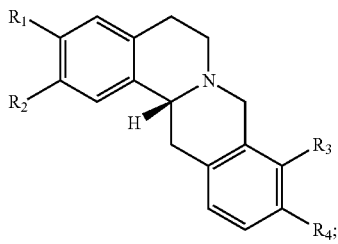

(IV)

and wherein $R_1$, $R_2$, $R_3$ and $R_4$ each independently or simultaneously represent a hydroxyl group or a methoxy group, with the proviso that at least one of $R_1$, $R_2$, $R_3$ and $R_4$ represents a methoxy group.

Referring to FIG. 10, in certain embodiments, the first alkaloid compound is a compound from selected from the group consisting of Tetrahydrocolumbamine and Scoulerine.

Referring to FIG. 10, in certain embodiments, the second alkaloid compound is a compound from selected from the group consisting of Tetrahydrocolumbamine, Tetrahydropalmatrubine and Tetrahydropalmatine.

In certain embodiments, the first alkaloid compound is Norlaudanosoline, the second alkaloid compound is 6-O-Methyl-norlaudanosline or Norreticuline and the O-methyltransferase is GFLOMT1 (SEQ. ID NO: 1592).

In certain embodiments, the first alkaloid compound is Norlaudanosoline, the second alkaloid compound is 6-O-Methyl-norlaudanosline and the O-methyltransferase is GFLOMT2 (SEQ. ID NO: 1593).

In certain embodiments, the first alkaloid compound is Norlaudanosoline, the second alkaloid compound is or Norcodamine and the O-methyltransferase is GFLOMT1 (SEQ. ID NO: 1592).

In certain embodiments, the first alkaloid compound is Norlaudanosoline, the second alkaloid compound is Norcodamine and/or Tetrahydropapaverine and the O-methyltransferase is GFLOMT2 (SEQ. ID NO: 1593).

In certain embodiments, the first alkaloid compound is 6-O-Methyl-norlaudanosline, the second alkaloid compound is Norreticuline and/or Norcodamine the methyltransferase is GFLOMT1 (SEQ. ID NO: 1592).

In certain embodiments, the first alkaloid compound is Norreticuline, the second alkaloid compound is Norlaudanine and the methyltransferase is GFLOMT6.

In certain embodiments, the first alkaloid compound is 6-O-Methyl-laudanosline, the second alkaloid compound is Reticuline and/or Codamine and the methyltransferase is GFLOMT1 (SEQ. ID NO: 1592).

In certain embodiments, the first alkaloid compound is 6-O-Methyl-laudanosline, the second alkaloid compound is Reticuline, Orientaline and/or Codamine and the methyltransferase is GFLOMT2 (SEQ. ID NO: 1593).

In certain embodiments, the first alkaloid compound is Reticuline, the second alkaloid compound is Codamine and the methyltransferase is GFLOMT2 (SEQ. ID NO: 1593).

In certain embodiments, the first alkaloid compound is Reticuline, the second alkaloid compound is Laudanine and/or Laudanosine and the methyltransferase is GFLOMT6 (SEQ. ID NO: 1597).

In certain embodiments, the first alkaloid compound is Norreticuline, the second alkaloid compound is Norcodamine and the methyltransferase is GFLOMT6.

In certain embodiments, the first alkaloid compound is Reticuline, the second alkaloid compound is Codamine and the methyltransferase is or GFLOMT6 (SEQ. ID NO: 1597).

In certain embodiments, the first alkaloid compound is 6-O-methyllaudanosoline, the second alkaloid compound is 6,7-O—O-dimethyllaudanosoline, and the methyltransferase is GLFOMT6 (SEQ. ID NO: 1597).

In certain embodiments, the first alkaloid compound is Norreticuline, the second alkaloid compound is tetrahydropapaverine and the methyltransferase is GFLOMT6 (SEQ. ID NO: 1597).

In further embodiments, the present disclosure provides, in at least one aspect, at least one embodiment of making an alkaloid compound, comprising:
(a) providing a first alkaloid compound;
(b) contacting the alkaloid compound with an O-methyltransferase under reaction conditions that permit methylation of the alkaloid compound to form a second alkaloid compound;

wherein the first alkaloid compound is selected from the group consisting of Scoulerine and Tetrahydrocolumbamine, and the second alkaloid compound is selected form the group consisting of Tetrahydropalmatrubine, Tetrahydropalmatine, Orientaline, Nororientaline and tetraydrocolumbamine.

In certain embodiments, the first alkaloid compound is Scoulerine, the second alkaloid compound is Tetrahydropalmatrubine and/or tetrahydropalmatine and the methyltransferase is GFLOMT1 (SEQ. ID NO: 1592).

In certain embodiments, the first alkaloid compound is Tetrahydrocolumbine, the second alkaloid compound is Tetrahydropalmatine and the methyltransferase is GFLOMT1 (SEQ. ID NO: 1592).

In certain embodiments, the first alkaloid compound is 6-O-methyl norlaudanosoline, the second alkaloid compound is Nororientaline and the methyltransferase is GFLOMT2 (SEQ. ID NO: 1593).

In certain embodiments, the first alkaloid compound is 6-O-methyl laudanosoline, the second alkaloid compound is Orientaline and the methyltransferase is GFLOMT2 (SEQ. ID NO: 1593).

In certain embodiments, the first alkaloid compound is Norlaudanosoline, the second alkaloid compound is Nororientaline and the methyltransferase is GFLOMT2 (SEQ. ID NO: 1593).

In certain embodiments, the first alkaloid compound is Scoulerine, the second alkaloid compound is Tetrahydropalmatrubine and/or tetrahydroplamatine and the methyltransferase is GFLOMT2 (SEQ. ID NO: 1593).

In certain embodiments, the first alkaloid compound is Tetrahydrocolumbine, the second alkaloid compound is Tetrahydropalmatine and the methyltransferase is GFLOMT1 (SEQ. ID NO: 1592).

In certain embodiments, the first alkaloid compound is Scoulerine, the second alkaloid compound is Tetrahydrocolumbamine and/or tetrahydropalmatine and the methyltransferase is GFLOMT6 (SEQ. ID NO: 1597).

In certain embodiments, the first alkaloid compound is Tetrahydrocolumbine, the second alkaloid compound is Tetrahydropalmatine and the methyltransferase is GFLOMT6 (SEQ. ID NO: 1597).

In certain embodiments, the first alkaloid compound is Scoulerine, the second alkaloid compound is Tetrahydrocolumbine and/or tetrahydropalmatrubine and the methyltransferase is GFLOMT7 (SEQ. ID NO: 1598).

In certain embodiments the first alkaloid compound is Tetrahydrocolumbamine, the second alkaloid compound is Tetrahydropalmatine and the methyltransferase is GFLOMT7 (SEQ. ID NO: 1598).

In further embodiments, mixtures of O-methyltransferases and/or N-methyltransferases may be used.

In certain embodiments, the first alkaloid compound is Norlaudanosoline, the second alkaloid compound is norcodamine and/or tetrahydropapaverine, and the methyltransferase is a mixture of GFLOMT1 (SEQ. ID NO: 1592) and GLFOMT2 (SEQ. ID NO: 1593).

In certain embodiments, the first alkaloid compound is Norlaudanosoline, the second alkaloid compound is codamine and/or reticuline, and the methyltransferase is a mixture of GFLOMT1 (SEQ. ID NO: 1592) and CNMT (e.g. SEQ. ID NO: 1327-SEQ. ID. NO: 1332 or SEQ. ID NO: 1749).

In certain embodiments, the first alkaloid compound is Norlaudanosoline, the second alkaloid compound is orientaline, laudanosine, codamine and/or reticuline, and the methyltransferase is a mixture of GFLOMT2 (SEQ. ID NO: 1593) and CNMT (e.g. SEQ. ID NO: 1327-SEQ. ID NO: 1332 or SEQ. ID NO: 1749).

In certain embodiments, the first alkaloid compound is Norlaudanosoline, the second alkaloid compound is orientaline, laudanosine, codamine and/or reticuline, and the methyltransferase is a mixture of GFLOMT2 (SEQ. ID NO: 1593), GFLOMT1 (SEQ. ID NO: 1592) and CNMT (e.g. SEQ. ID NO: 1327-SEQ. ID NO: 1332 or SEQ. ID NO: 1749).

In certain embodiments, the first alkaloid compound is Norlaudanosoline, the second alkaloid compound is norcodamine and/or tetrahydropapaverine, and the methyltransferase is a mixture of GFLOMT1 (SEQ. ID NO: 1592) and GLFOMT6 (SEQ. ID NO: 1597).

In certain embodiments, the first alkaloid compound is Norlaudanosoline, the second alkaloid compound is norientaline, norcodamine and/or tetrahydropapaverine, and the methyltransferase is a mixture of GFLOMT2 (SEQ. ID NO: 1593) and GLFOMT6 (SEQ. ID NO: 1597).

In certain embodiments, the first alkaloid compound is Norlaudanosoline, the second alkaloid compound is nororientaline, norcodamine and/or tetrahydropapaverine, and the methyltransferase is a mixture of GFLOM1 (SEQ. ID NO: 1592), GFLOMT2 (SEQ. ID NO: 1593) and GLFOMT6 (SEQ. ID NO: 1597).

In certain embodiments, the first alkaloid compound is Norlaudanosoline, the second alkaloid compound is reticuline, codamine, norcodamine, laudanine and/or laudanosine, and the methyltransferase is a mixture of GFLOM1 (SEQ. ID NO: 1592), GFLOMT6 (SEQ. ID NO: 1597) and CNMT (e.g. SEQ. ID NO: 1327-SEQ. ID NO: 1332 or SEQ. ID NO: 1749).

In certain embodiments, the first alkaloid compound is Norlaudanosoline, the second alkaloid compound is orientaline, reticuline, codamine, laudanine and/or laudanosine, and the methyltransferase is a mixture of GFLOM1 (SEQ. ID NO: 1592), GFLOMT2 (SEQ. ID NO: 1593), GFLOMT6 (SEQ. ID NO: 1597) and CNMT (e.g. SEQ. ID NO: 1327-SEQ. ID NO: 1332 or SEQ. ID NO: 1749).

In certain embodiments, the first alkaloid compound is Norlaudanosoline, the second alkaloid compound is reticuline, codamine, norcodamine, laudanine and/or laudanosine, and the methyltransferase is a mixture of GFLOM1 (SEQ. ID NO: 1592), GFLOMT6 (SEQ. ID NO: 1597) and CNMT (e.g. SEQ. ID NO: 1327-SEQ. ID NO: 1332; or SEQ. ID NO: 1749).

The foregoing embodiments of the present disclosure may be performed in-vitro or in-vivo.

In embodiments where in-vitro reactions are performed, the first alkaloid is brought in contact with catalytic quantities of the OMT and/or NMT enzymes under reaction conditions permitting an enzyme catalyzed chemical conversion of the first alkaloid under in vitro reaction conditions. Under such in vitro reaction conditions the initial reaction constituents are provided in more or less pure form and are mixed under conditions that permit the requisite chemical reactions to substantially proceed. Substantially pure forms of the initial alkaloid may be purchased. (S)-Reticuline, for example, may be purchased (e.g. from Santa Cruz Biotechnology Inc.) as a substantially pure chemical compound, chemically synthesized from precursor compounds, or isolated from natural sources including *Papaver somniferum* and other members of the Papaveraceae, Lauraceae, Annonaceae, Euphorbiaceae or Moraceae families of plants comprising such compounds as desired. In accordance herewith, more or less pure forms of the enzymes may be isolated from natural sources, including, but not limited to, *Papaver somniferum, Papaver bracteatum* and *Papaver rhoeas*, or they may be prepared recombinantly, or synthetically.

In embodiments where in-vivo reactions are performed, a first alkaloid is brought in contact with catalytic quantities of one or more of the OMT and/or NMT enzymes under reaction conditions permitting an enzyme catalyzed chemical conversion of the alkaloid derivative under in vivo reaction conditions. Under such in vivo reaction conditions living cells are modified in such a manner that they produce can convert the first alkaloid. In certain embodiments, the living cells are microorganisms, including bacterial cells and fungal cells. In other embodiments, the living cells are multicellular organisms, including plants and plant cell cultures.

In one embodiment, the living cells are selected to be host cells not naturally capable of capable of producing the second alkaloid. In another embodiment, the host cells are naturally capable of producing the second alkaloid but at levels that are lower than desirable. Such cells include, without limitation, bacteria, yeast, other fungal cells, plant cells, or animal cells. In embodiments where mixtures of enzymes are used cells comprising these enzymes may be mixed.

EXAMPLES

Hereinafter are provided examples of specific embodiments of the present disclosure, as well as embodiments representing the compositions of the present disclosure. The examples are provided for illustrative purposes only, and are not intended to limit the scope of the present disclosure in any way.

Example 1—Isolation of cDNA Candidate Polynucleotides from 20 Plant Species

The Trizol method was used to extract total RNA from plant organs and tissues (Chomczynski and Sacchi, 1987). When the polysaccharide and polyphenolic content was high, such as in roots or rhizomes, a modified CTAB method was used (Desgagné-Penix et al., 2010). The quality and quantity of isolated total RNA were evaluated on the basis of UV absorption ratios (i.e. 260/280 nm and 260/230 nm). All the samples showed a 260/280 nm ratio of between 1.9 and 2.1, and a 260/230 nm ratio in the range of 2.0 to 2.5.

Poly(A)+ RNA purification, cDNA library preparation, emulsion-based PCR (emPCR) and sequencing was performed at the McGill University and Génome Québec Innovation Centre (Montréal, Canada). The RNA content in all samples was quantified using a NanoDrop ND-1000 spectrophotometer (Thermo Scientific). RNA samples were further analyzed using an RNA 6000 Nano chip on a BioAnalyzer 2100 (Agilent Technologies) to validate RNA quality. Only samples with a BioAnalyzer RNA Integrity Number (RIN) of 7.5 or greater were used for sequencing. Poly(A)$^+$RNA was purified from 20-40 µg of total RNA by two rounds of selection using oligo (dT) attached to magnetic beads and a Dynabeads mRNA Purification kit (Invitrogen). The cDNA libraries for Roche-454 pyrosequencing were constructed from 200 ng of mRNA using a cDNA Rapid Library kit (Roche) and subsequently amplified by emPCR as per the manufacturer's instructions. After amplification, the DNA carrying beads for each library were loaded onto one-half of a PicoTiterPlate and subjected to Roche-454 GS-FLX Titanium pyrosequencing. Image and signal processing of the raw output data was performed using GS Run Processor. Sequence reads with high-quality scores were written into Standard Flowgram Format (SFF) files.

The cDNA libraries for Illumina GA sequencing were constructed from 10 µg of total RNA using the TruSeq Stranded mRNA Sample Prep Kit (Illumina) according to the manufacturer's instructions. The quality and average length of cDNAs in each library were determined using a High Sensitivity DNA (Agilent Technologies) chip on a 2100 Bioanalyzer. For Illumina GA sequencing, 7 pmol of each library containing cDNA with lengths from 600 to 1200 base pairs (bp) were loaded into one lane of the flow cell to generate approximately 750,000 clusters per mm$^2$. HCS 1.4 and CASAVA 1.6-1.8 suite were used to obtain base calls and raw fastq reads.

Quality scores and header information were extracted from SFF files generated from the 454 data. The pre-processing pipeline included several cleaning procedures, including clipping of adapter/primer sequences and window-based trimming of reads with Phred quality scores of less than 22. Low-complexity regions, including homopolymers were masked along with repeat regions identified based on similarity to the following: the RepBase14 database (Jurka et al., 2005), the Viridiplantae subset of NCBI reference sequences (Refseq), and the TIGR plant repeat database (Ouyang and Buell, 2004). Ribosomal RNA (rRNA) and ribosomal protein reference sets for related species were downloaded from NCBI and SILVA databases (Pruesse et al., 2007). Reads identified as rRNA and ribosomal protein sequences, and those shorter than 100 bp (not including masked regions) were removed from each 454 database. The Scylla component of the Paracel Filtering Package (PFP) (Paracel Inc, Pasadena, Calif.) was used to perform these steps.

Initial quality assessment for Illumina GA sequence data was based on FastQC www.bioinformatics.babraham.ac.uk/projects/fastqc) statistics, and Cut-adapt (Martin and Wang, 2011) was used for adapter/primer trimming. Trimmed reads were further subjected to quality score conversion, trimming of reads with Phred quality scores of less than 25, and removal of read pairs with at least one member shorter than 35 bp using scripts written in-house. Read were also trimmed at the 5' end by 12-14 bp to account for bias associated with random priming. rRNA and ribosomal protein content was monitored by mapping the raw reads against the reference sets downloaded from NCBI and SILVA databases. No filtering step was applied if the composition was not substantial.

For 454 GS-FLX sequencing, assemblies of cleaned 454 sequence data were generated using MIRA (version 3.2) (Chevreux et al. 2004). The pre-processing functions in MIRA (Chevreux et al. 2004) were disabled and analyses were performed using the 'accurate' setting. Other de novo assemblers, Paracel Transcript Assembler (Paracel Inc), CLC assembly cell (CLC bio, Cambridge Mass.), and Newbler v2.3 (Margulies et al., 2005) were also evaluated by comparing assembly statistics. MIRA produced the largest number of contigs over 1000 bp using the highest proportion of 454 reads.

Short-read Illumina GA data were assembled using Velvet-Oases v0.1.16 (Zerbino and Birney, 2008). Optimal assembly of contigs in each database and representing a wide dynamic range of gene expression was acquired using a combined k-mer assembly approach. The pipeline generated eight parallel Oases runs for each paired-end read set using incremental k-mer settings increasing by units of 5 between 37 to 67. The generation of multiple copies of similar transcripts was expected among the different k-mer runs when merging the eight assemblies. The clustering tool CD-HIT-EST (Li and Godzik, 2006) was used to reduce redundancy by clustering nearly identical (greater than 99%) transcripts and extracting the longest representative within each cluster. The non-redundant pool of transcripts was further assembled using CAP3 (Huang and Madan, 1999) to combine contigs with significant overlaps (minimum 95% identity over at least 50 bp). Final assemblies were completed after contigs of less than 300 bp were discarded.

Annotation of the 20 assembled transcriptome datasets was performed using the Magpie Automated Genomics Project Investigation Environment (MAGPIE) (Gaasterland and Sensen, 1996). MAGPIE automates sequence similarity searches against major public and internal target databases. TimeLogic Decypher Biocomputing systems www.timelogic.com were used to significantly accelerate similarity searches. Specifically, the Time-Logic Tera-BLAST algorithm was used to compare transcripts to the NCBI databases NR (non-redundant) and the viridiplantae subset of RefSeq (Pruitt et al., 2007). An expected e-value of 1e-3 and a minimum alignment length of 30 bp were used. To obtain motif-level information, accelerated Hidden Markov Model (HMM) searches were performed against local instances of Interpro HMM libraries at an e-value of 1e-10. The NCBI Conserved Domain Database (CDD) was also queried using RPS-BLAST for additional annotation information.

To coordinate all search results for each contig, MAGPIE ranked individual hits into three tiers of confidence. For BLAST results, e-value cutoffs were set at 1e-35, 1e-15, and 1e-5 for evidence levels 1, 2 and 3 respectively. For HMM results, e-value cutoffs were 1e-20, 1e-14 and 1e-10 at percentage similarity requirements of 65, 45 and 25%, respectively. Putative functional descriptions were assigned to each contig by performing a weighted summary of search result annotations. Summaries were based on word frequency, lexical complexity and word length, in addition to the level and type of evidence, and the taxonomic distance between the subject and the query species. GO annotations and EC numbers were compiled from GIDs extracted from level-1 evidence and attached to individual contigs as additional functional information. Contigs were subsequently cross-mapped to one another based on common GO terms and level-1 evidence. As a step towards the incorporation of metabolomics data, putative transcript data was mapped to KEGG metabolic pathways based on EC numbers. A summary page holding all evidence and annotation was generated for each contig in MAGPIE.

Annotated contigs were available for further analysis after the assembly and annotation of each sequence dataset. ESTScan (Lottaz et al., 2003) is a statistical hidden Markov model (HMM) program that can be used to discover patterns and was used for CDS detection. A refined HMM model was built using a set of full-length coding sequences for training. To determine the training set, the annotation evidence for each contig within an assembly was examined on all six open reading frames. The frame with the longest length of annotated sequence was scanned further. If the length of annotation within the selected frame was greater than 75% of the original contig length and contained putative start and stop codons, this frame was saved as a training set member. To ensure that the selected CDS has the maximum possible length, another scan was extended to flanking regions to search for possible start and stop codons.

After the double scanning was applied to every contig in an assembly, a set of putative full-length coding sequences was collected. This full-length coding sequence dataset was used to train ESTScan to build the HMM model (Iseli et al., 1999). After building the model, ESTScan was applied again to predict a putative CDS for every contig of the assembly. The CDS dataset from ESTScan could contain partial coding regions; thus, scanning of the original contig and annotation was repeated for every CDS generated. When both start and stop codons were found in the original contig and the annotation was longer than 75% of the original contig length, this putative CDS was retained as a full-length putative CDS. In contrast, partial putative coding regions were removed. The full-length putative CDS dataset was then combined with the full-length coding region dataset used to train the HMM model. Duplicated sequences were removed to generate the final predicted CDS dataset. To conservatively estimate the intersect between predicted full-length CDS sets generated by 454 and Illumina, Mega BLAST (Zhang et al, 2000) was used to compare respective sets at an e-value cutoff of 0.

Gene expression levels were determined by quantifying the observed read abundance. Raw read counts were extracted from assembly files for each contig in the case of the 454 assemblies. For Illumina GA data, counts were estimated by re-mapping raw short reads to the assembled contigs using Bowtie (Langmead et al., 2009). The RNA-Seq by Expectation-Maximization (RSEM) package (Li and Dewey, 2011) was used to resolve ambiguous mappings and to perform final quantifications. Only paired-end reads that mapped to a common contig were considered. Normalization was done by calculating FPKM values (Fragments Per Kilobase of exon model per Million mapped reads) for each contig.

Example 2—Isolating cDNA Candidate Polynucleotides Encoding N-Methyltransferases Involved in Benzylisoquinoline Alkaloid Biosynthesis More than 2,500 BIAs, many of which possess potent pharmacological properties, have been identified in plants belonging mostly to the families Papaveraceae, Ranunculaceae, Berberidaceae and Menispermaceae (Ziegler and Facchini, 2008). Many of the enzymes involved in BIA biosynthesis have been identified from a limited number of plants including opium poppy (*Papaver somniferum*) and Japanese goldthread (*Coptis japonica*), yet the majority of catalysts responsible for the immense structural diversity of BIAS in other plants have not been characterized. Tapping into the vast biosynthetic potential of plants requires access to genes from a variety of species. The transcriptome databases from 20 BIA-producing species represent such a repository of unique biosynthetic genes responsible for the diverse alkaloid content of these plants. Based on the categorization of known BIA biosynthetic enzymes into discrete protein families (e.g. cytochromes P450, O- and N-methyltransferases, various NADPH-dependent reductases, FAD-linked oxidoreductases, acyl-CoA-dependent acetyltransferases and 2-oxoglutarate-dependent dioxygenases) numerous orthologous and paralogous candidate genes can be selected from these databases for functional characterization.

The utility of NGS-based transcriptome databases from related plant species for the identification of novel biosynthetic enzymes is shown by focusing on N-methylation as a common functional group modification in BIA metabolism. Three alkaloid type-specific N-methyltransferases (NMTs) have been been characterized: coclaurine N-methyltransferase (CNMT), tetrahydroprotoberberine N-methyltransferase (TNMT) and pavine N-methyltransferase (PavNMT) (FIG. 1) (Liscombe et al., 2009). (+)-Magnoflorine is an antimicrobial alkaloid produced in several plant species via the N-methylation of (S)-corytuberine (Minami et al., 2008). Although the enzyme responsible for the formation of the quaternary ammonium in (+)-magnoflorine has not been identified (FIG. 1), CNMT from *Coptis japonica* was reported to N-methylate a broad range of substrates including corytuberine (Minami et al., 2008). Among the 20 BIA-producing plant species listed in TABLES 2-4, *Glaucium flavum* is known to accumulate substantial quantities of (+)-magnoflorine (Novák and Slavík, 1974) suggesting that an efficient corytuberine N-methyltransferase is represented among the NMT homologs in the transcriptome database for this plant. A phylogenetic tree was constructed using predicted amino acid sequences of the NMT homologs from all 20 BIA-producing species (TABLES 2-4) and several functionally characterized NMTs from related plants (FIG. 2). Six full-length paralogs distributed in three different NMT subclades were identified from the *G. flavum* 454 and Illumina GA sequence databases. Based on the extensive sequence similarity, most of the candidate genes are expected to encode NMTs involved in BIA metabolism. However, empirical enzyme characterization is required to confirm precise catalytic function. For example, GfNMT1 is the most likely CNMT functional ortholog in *G. flavum*, GfNMT2 and GfNMT3 are expected to exhibit TNMT activities with unique or overlapping substrate preferences, and GfNMT4 could function as a PavNMT (FIG. 2). In contrast, the predicted amino acid sequences of GfNMT5 and GfNMT6 are sufficiently distinct to suggest unique substrate specificities. Considering that (S)-corytuberine exhibits structurally similarity to the CNMT substrate (S)-coclaurine, GfNMT5 or GfNMT6 are candidates for a predicted corytuberine N-methyltransferase in *G. flavum* (FIG. 1). Gene triage is conducted for selecting priority candidates from large gene families.

Example 3—Confirming an Improved Polynucleotide Sequence Encoding N-Methyltransferases Involved in Benzylisoquinoline Alkaloid Synthesis Less than 2% of exogenous (R,S)-norlaudanosoline was converted to sanguinarine via a pathway of 10 genes from opium poppy (*Papaver somniferum*) re-assembled in yeast (*Saccharomyces cerevisiae*) (Fossati et al., 2014). An improvement in the conversion efficiency of the pathway can be achieved by substituting one or more specific opium poppy genes, with similar variants or known or unknown function from another plant species. More specifically, the opium poppy enzymes cheilanthifoline synthase (CYP719A25) and stylopine synthase (CYP719A20) can be replaced with SEQ. ID NO: 262 and SEQ. ID NO: 264, respectively, with the resulting yeast strain demonstrating an improvement in the conversion of exogenous (R,S)-norlaudanosoline to sanguinarine. Similarly, opium poppy tetrahydroprotoberberine cis-N-methyltransferase (TNMT) can be replaced with SEQ. ID NO: 445, resulting in further improvement in the conversion efficiency of the yeast strain.

Mining of transcriptome databases for the selected plant species generates hundreds of biosynthetic genes encoding enzymes with novel catalytic activities and variants with similar functions, but different biochemical features. Genes encoding variants display improved expression characteristics in plants and microorganisms, providing metabolic engineering options for the optimization of synthetic biosystems designed to produce high-value plant metabolites. The use of this technology, employing various combinations and permutations of biosynthetic genes to engineer multistep biosynthetic pathways in microorganisms, also accelerates the discovery of novel enzymes, and the reconstruction and optimization of natural and unnatural product pathways based on combinatorial biochemistry.

Various studies have partially reconstituted other plant natural product pathways in *Escherichia coli* or yeast (*Saccharomyces cerevisiae*) leading to the formation of taxadiene, a key isoprenoid intermediate in taxol biosynthesis, amorphadiene, the sesquiterpene olefin precursor to artemisinin (Martin et al., 2003), artemisinic acid, the immediate precursor to artemisinin (Ro et al., 2008), the diterpene fragrance precursors cis-abienol (Zerbe et al., 2012) and sclareol (Caniard et al., 2012). Nevertheless, the deployment of most plant metabolic pathways in microbial hosts still requires the isolation and functional characterization of many unknown biosynthetic genes. Even when all biosynthetic genes required for the formation of a specific compound have been isolated from one plant and reconstituted in a microorganism, the specific catalytic characteristics of each enzyme can be inappropriate for the efficient operation of the metabolic pathway in a heterologous system. In such cases, the overall metabolic flux will be limited by the enzyme step with the lowest catalytic efficiency. The availability of enzyme variants from a wide variety of plant species, as described in this disclosure, provides a possible empirical solution to such metabolic engineering bottlenecks.

Example 4—Identifying cDNA Candidate Polynucleotides Encoding O-Methyltransferases Involved in Benzylisoquinoline Alkaloid Biosynthesis Libraries containing cDNA sequences of 20 BIA-producing plant species were prepared and sequenced as described in Example 1. Within these libraries seven homologues of characterized O-methyltransferases (OMTs) involved in BIA biosynthesis were isolated from assembled 454 and Illumina GA databases (Xiao et al, 2013) of *Glaucium flavum* (GFLOMTs). The candidate selection strategy was based on a cutoff of 35% overall amino acid sequence identity with at least one functionally characterized OMT involved in BIA biosynthesis. Phylogenetic analysis showed that GFLOMT1-4 and GFLOMT6 formed separate clades with known OMTs (FIG. 3), whereas GFLOMT5 and GFLOMT7 formed a new clade. GFLOMT1 shares 77 and 71% amino acid sequence identities with Ps4'OMT2 from opium poppy and Cj4'OMT from *Coptis japonica*, respectively. GFLOMT2 shows 80 and 70% sequence identities with Ps6OMT from opium poppy and Cj6OMT from *C. japonica*, respectively. GFLOMT3 shares 63% sequence identities with Ps7OMT from opium poppy and GFLOMT4 shows 38% sequence identity with CjCoOMT from *C. japonica*. GFLOMT6 shares 60 and 63% sequence identities with PsSOMT from opium poppy and CjSOMT from *C. japonica*, respectively. In contrast, GFLOMT5 and GFLOMT7 display only 42 and 44% sequence identity with the nearest neighbor CjSOMT from *C. japonica*, respectively.

Example 5—Expression of O-methyltransferases

Full-length cDNAs for the seven GFLOMT candidates (see: Example 6) were cloned into the pRSETA expression vector with an N-terminal His_tag translational fusion and expressed in *E. coli*. Recombinant GFLOMTs were purified from total protein extracts using a cobalt-affinity resin. All purified recombinant enzymes displayed molecular weight values corresponding to expected protein sizes, as determined by SDS-PAGE (FIG. 4)

Example 6—Substrate Specificity of O-Methyltransferases

Substrate specificity of the seven FLOMT's was assessed using a range of different alkaloid substrates, notably (R,S)-norlaudanosine; (R,S)-6-O-Methylnorlaudanosoline; (R,S)-6-O-Methyllaudanosoline; (R,S)-Norreticuline; (S)-Reticuline; (R,S)-Scoulerine; and (R,S)-Tetrahydrocolumbamine. Results are shown in TABLE 5. In the presence of SAM, GFLOMT1 showed differential activity with all seven substrates. Norlaudanosoline was the preferred substrate displaying 96% conversion in the standard OMT assay, however, 6-O-methylnorlaudanosoline (87%) and 6-O-methyllaudanosoline (68%) were also efficiently converted. Scoulerine (32%), tetrahydrocolumbamine (19%), and reticuline (6%) were also accepted, but with relatively lower conversion efficiencies. Norlaudanosoline was also the best substrate for GFLOMT2 (100%), whereas 6-O-methylnorlaudanosoline (1%) and 6-O-methyllaudanosoline (14%) were not efficiently converted. In further contrast to GFLOMT1, scoulerine (75%), tetrahydrocolumbamine (32%), and reticuline (22%) were accepted with relatively higher conversion efficiencies. Scoulerine was the preferred substrate for GFLOMT6 (100%), with reticuline (97%) and tetrahydrocolumbamine (90%) also efficiently converted, and norreticuline (36%) and 6-O-methyllaudanosoline (23%) accepted at moderate levels. GFLOMT6 did not accept norlaudanosoline or 6-O-methylnorlaudanosoline. GFLOMT7 showed relatively low activity with scoulerine (12%) and tetrahydrocolumbamine (8%), but did not accept other BIAs. GFLOMT3, GFLOMT45, and GFLOMT5 did not show activity with any of the tested substrates. Kinetic analyses with preferred substrates yielding single reaction products showed that the three most effective GFLOMTs followed the Michaelis-Menton model. GFLOMT1 exhibited a $K_m$ of 12 µM for 6-O-methylnorlaudanosoline, GFLOMT2 showed a $K_m$ of 15 µM for norlaudanosoline, GFLOMT6 showed a $K_m$ of 22 µM for scoulerine, Catalytic efficiencies ($k_{cat}/K_m$) were relatively high for all three conversions.

Example 7—In-Vitro Reaction Products Formed by O-Methyltransferases

The reaction products formed using GFLOMT1, GFLOMT2, GFLOMT6 and GFLOMT7 were analyzed. Enzyme assays were subjected to positive-mode electrospray ionization (ESI[+]) LC-MS/MS for reaction product characterization, including collision-induced dissociation (CID) fragmentation analysis. ESI[+]-CID of 1-benzylisoquinoline and protoberberine alkaloids at low ionization energy yields isoquinoline and/or benzyl moieties as major ion fragments. Using the ESI[+]-CID spectra of authentic standards (TABLE 6), the identity of recombinant GFLOMT reaction products was determined (TABLE 7). Positions of new O-methyl groups could be inferred from the increased m/z (in multiples of 14 Da) of dissociated isoquinoline and benzyl ion fragments even in the absence of authentic standards, although most were available.

GFLOMT1

Incubation of GFLOMT1 with norlaudanosoline (m/z 288) yielded two major peaks with m/z 302 at 2.62 min and m/z 316 at 2.95 min (FIG. 5A), suggesting single and double O-methylation events, respectively. The parent ion of m/z 302 produced an ESI[+]-CID spectrum corresponding to authentic 6-O-methylnorlaudanosoline, whereas the parent ion of m/z 316 produced an ESI[+]-CID spectrum matching that of norreticuline. Assays containing GFLOMT1 and 6-O-methylnorlaudanosoline (m/z 302) generated major and minor products of m/z 316 and m/z 330, with ESI[+]-CID spectra corresponding to norreticuline and norcodamine, respectively (FIG. 5B). Although an authentic standard for norcodamine was not available, compound identity could be inferred. Compared with the ESI[+]-CID spectrum of 6-O-methylnorlaudanosoline, which displays the fragment ions m/z 178 (isoquinoline moiety) and m/z 123 (benzyl moiety), the m/z 330 reaction product yielded major fragment ions of m/z 178 and m/z 151 (increase of 28 Da), the latter of which corresponds to a 3- and 4-O-methylated benzyl moiety. Incubation of GFLOMT1 with 6-O-methyllaudanosoline (m/z 316) yielded major and minor products with m/z 330 at 2.99 min and m/z 344 at 3.17 min, corresponding to single and double O-methylation events, respectively (FIG. 5C). The m/z-330 parent ion produced an ESI[+]-CID spectrum corresponding to authentic reticuline, whereas the double O-methylated m/z-344 parent ion yielded an ESI[+]-CID spectrum matching that of codamine. In assays containing GFLOMT1 and reticuline, a minor product of m/z 344 with an ESI[+]-CID spectrum corresponding codamine was also produced (FIG. 5D). The major and minor products resulting from the incubation of GFLOMT1 with scoulerine showed parent masses of m/z 342 and m/z 356, with ESI[+]-CID spectra corresponding to tetrahydropalmatrubine and tetrahydropalmatine (FIG. 5E). An authentic standard for tetrahydropalmatrubine was not available, however, product identification was inferred from the 14-Da increase in the isoquinoline moiety of scoulerine (m/z 178) to m/z 192. In assays containing GFLOMT1 and tetrahydrocolumbine a minor product was generated with a parent mass of m/z 356 and an ESI[+]-CID spectrum corresponding to tetrahydropalmatine (FIG. 5F).

GFLOMT2

GFLOMT2 efficiently converted norlaudanosoline (m/z 288) to a product with m/z 302, which yielded an ESI[+]-CID spectrum corresponding to 6-O-methylnorlaudanosoline (FIG. 6A). In contrast, GFLOMT2 incubated with 6-O-methylnorlaudanosoline generated a minor product with m/z 316 (FIG. 6B), which was inferred as nororientaline based on the detection of major fragment ions of m/z 178 (isoquinoline moiety) and m/z 137 (3'-O-methylated benzyl moiety). The different retention time compared with norreticuline (i.e. 4'-O-methylated 6-O-methylnorlaudanosoline) confirmed 3'-rather than 4'-O-methylation. Incubation of GFLOMT2 with 6-O-methyllaudanosoline (m/z 316) yielded three products with m/z 330 at 2.85 min, m/z 330 at 2.98 min, and m/z 344 at 3.15 min, indicating both single and double O-methylation events (FIG. 6C). The identity of the m/z-330 parent ion at 2.85 min was inferred as orientaline based on the detection of major fragment ions of m/z 192 (isoquinoline moiety) and m/z 137 (3'-O-methylated benzyl moiety). The different retention time compared with reticuline (i.e. 4'-O-methylated 6-O-methyllaudanosoline and the m/z-330 parent ion at 2.98 min) confirmed 3'-rather than 4'-O-methylation. The double O-methylation product corresponded to a parent ion of m/z-344 parent ion yielded an ESI[+]-CID spectrum corresponding to codamine. The minor GFLOMT2 reaction product with reticuline showed a parent mass of m/z 344 and ESI[+]-CID spectrum corresponding to codamine (FIG. 6D). Incubation of GFLOMT2 with scoulerine (m/z 328) yielded major and minor products with m/z 342 and m/z 356, identified as tetrahydropalmatrubine and tetrahydropalmatine, respectively (FIG. 6E). The reaction product of GFLOMT2 incubated with tetrahydrocolumbine showed a parent mass of m/z 356, which was also identified as tetrahydropalmatine (FIG. 6F).

FLOMT6

Incubation of GFLOMT6 with 6-O-methyllaudanosoline (m/z 316) yielded a reaction product with m/z 330 (FIG. 7A), which was inferred as 6,7-O,O-dimethyllaudanosoline based on ESI[+]-CID spectrum and a unique retention time. Compared with the ESI[+]-CID spectrum of 6-O-methyllaudanosoline, which shows major fragment ions of m/z 192 and m/z 123, the m/z 330 product yielded fragment ions of m/z 206 (7-O-methylated isoquinoline moiety) and m/z 123 (unchanged benzyl moiety). Incubation of GFLOMT6 with norreticuline (m/z 316) yielded two major and one minor reaction products with m/z 330 at 3.16 min, m/z 330 at 3.25 min, and m/z 344 at 3.43 min (FIG. 7B), corresponding to single and double O-methylation events. Identity of the m/z-330 parent ion at 3.16 min was inferred as norcodamine based on the ESI[+]-CID spectrum and unique retention time. The m/z-330 parent ion at 3.25 min produced and ESI[+]-CID spectrum corresponding to norlaudanine. The minor double O-methylation product with m/z 344 produced an ESI[+]-CID spectrum matching that of tetrahydropapaverine. GFLOMT6 efficiently converted reticuline (m/z 330) to three products with m/z 344 at 3.17 min, m/z 344 at 3.24 min, and m/z 358 at 3.43 min (FIG. 7C), indicating single and double O-methylation events. The m/z-344 parent ions at 3.17 and 3.24 min yielded ESI[+]-CID spectra corresponding to codamine and laudanine. The double O-methylation product with a parent ion of m/z 358 generated an ESI[+]-CID spectrum matching that of laudanosine. GFLOMT6 efficiently converted scoulerine (m/z 328) to two major reaction products with m/z 342 at 3.29 min, and m/z 356 at 3.59 min (FIG. 7D), corresponding to single and double O-methylation events, respectively. The m/z-342 parent ion produced an ESI[+]-CID spectrum corresponding to tetrahydrocolumbamine, whereas the m/z-356 parent ion yielded an ESI[+]-CID spectrum matching that of tetrahydropalmatine. Incubation of GFLOMT6 with tetrahydrocolumbine (m/z 342) generated a major product with m/z 356 and an ESI[+]-CID spectrum corresponding to tetrahydropalmatine (FIG. 7E).

FLOMT7

Incubation of GFLOMT7 with scoulerine (m/z 328) yielded two minor reaction products with m/z 342 at 3.33 min and m/z 342 at 3.44 min (FIG. 7F) with ESI[+]-CID spectra corresponding to tetrahydrocolumbine (i.e. methylated benzyl moiety of scoulerine) and tetrahydropalmatrubine (methylated isoquinoline moiety of scoulerine), respectively. The reaction product of GFLOMT7 incubated with tetrahydrocolumbine (m/z 342) generated a reaction product with m/z 356 and an ESI[+]-CID spectrum corresponding to tetrahydropalmatine (FIG. 7G).

Example 8—In Vivo Reaction Products Formed by O-Methyltransferases (R,S)-Norlaudanosoline was fed to mixed cultures of E. coli harboring different combinations and permutations of pGFLOMT1, pGFLOMT2, pGFLOMT6, and pCNMT to determine the in vivo efficiency of each OMT with both N-methylated and N-desmethyl 1-benzylisoquinolines (FIG. 8). Norlaudanosoline was not recovered in ethyl acetate extractions. The empty vector control showed that E. coli was inherently incapable of transforming norlaudanosoline to other BIAs (FIG. 8A). Transformation product identifications were determined using the ESI[+]-CID spectra of authentic standards and inferences described above, which are generally not repeated below.

Incubation of an E. coli strain harboring pGFLOMT1 with norlaudanosoline (m/z 288) yielded one compound identified as norcodamine (m/z 330) (FIG. 8B). In contrast, incubation of an E. coli strain harboring pGFLOMT2 with norlaudanosoline generated three products with m/z 316 at 2.85 min, m/z 330 at 3.15 min, and m/z 344 at 3.42 min (FIG. 8C) corresponding to nororientaline, norcodamine, and tetrahydropapaverine, respectively. Incubation of mixed E. coli strains harboring pGFLOMT1 and pGFLOMT2 with norlaudanosoline yielded compounds with m/z 330 at 3.15 min and m/z 344 at 3.42 min (FIG. 8D) corresponding to norcodamine and tetrahydropapaverine, respectively. Addition of an E. coli strain harboring pCNMT to this series altered the profile of products formed in all pGFLOMT combinations. Incubation of mixed E. coli strains harboring pGFLOMT1 and pCNMT with norlaudanosoline compounds with m/z 330 at 2.99 min and m/z 344 at 3.17 min identified as reticuline and codamine (FIG. 8E). Incubation of mixed E. coli strains harboring pGFLOMT2 and pCNMT with norlaudanosoline resulted in four compounds with m/z 330 at 2.85 min, m/z 330 at 2.98 min, m/z 344 at 3.16 min, and m/z 358 at 3.4 min corresponding to orientaline, reticuline, codamine, and laudanosine (FIG. 8F). Incubation of mixed E. coli strains harboring pGFLOMT1, pGFLOMT2, and pCNMT with norlaudanosoline also produced orientaline, reticuline, codamine, and laudanosine, but with an apparently higher yield compared with incubations lacking one of the strains (FIG. 8G).

Incubation of mixed E. coli strains harboring of pGFLOMT1 and pGFLOMT6 with norlaudanosoline yielded two products with m/z 330 at 3.14 min and m/z 344 at 3.43 min, corresponding to norcodamine and tetrahydropapaverine, respectively (FIG. 8H). Incubation of mixed E. coli strains harboring pGFLOMT2 and pGFLOMT6 with norlaudanosoline generated three compounds with m/z 316 at 2.87 min, m/z 330 at 3.14 min, m/z 344 at 3.43 min, identified as nororientaline, norcodamine, and tetrahydropapaverine, respectively (FIG. 8I). Combining E. coli strains harboring pGFLOMT1, pGFLOMT2, and pGFLOMT6, and incubating with norlaudanosoline only changed the relative abundance of nororientaline, norcodamine, tetrahydropapaverine (FIG. 8J), compared with the absence of pGFLOMT1 (FIG. 8I). However, addition of an E. coli strain harboring pCNMT to this series altered the profile of products generated via all pGFLOMT combinations. Incubation of mixed E. coli strains harboring pGFLOMT1, pGFLOMT6, and pCNMT, and incubation with norlaudanosoline produced five compounds with m/z 330 at 2.99 min, m/z 330 at 3.16 min, m/z 344 at 3.18 min, m/z 344 at 3.24 min, and m/z 358 at 3.42 min, identified as reticuline, norcodamine, codamine, laudanine, and laudanosine, respectively (FIG. 8K). Mixed E. coli strains harboring pGFLOMT2, pGFLOMT6, and pCNMT with norlaudanosoline yielded compounds with m/z 330 at 2.88 min, m/z 330 at 3 min, m/z 344 at 3.16 min, m/z 344 at 3.23 min, and m/z 358 at 3.42 min, corresponding to orientaline, reticuline, codamine, laudanine, and laudanosine, respectively (FIG. 8L). Finally, incubation of mixed E. coli strains harboring pGFLOMT1, pGFLOMT2, pGFLOMT6, and pCNMT with norlaudanosoline produced the same five compounds, but with an apparently higher yield than incubations lacking the E. coli strain harboring pGFLOMT1 (FIG. 8M).

While the present disclosure has been described with respect to what are presently considered to be the preferred examples, it is understood that the disclosure is not limited to the disclosed examples. To the contrary, the disclosure is intended to cover various modifications and equivalent arrangements included within the spirit of the appended claims.

All publications, patents and patent applications are incorporated by reference in their entirety to the same extent as if each individual publication, patent or patent application was specifically indicated to be incorporated by reference in its entirety.

TABLE 1

| Enzyme Name | Abbreviation | Exemplary SEQ ID NO (polynucleotide/amino acid) | Exemplary Substrate/Product |
|---|---|---|---|
| Norcoclaurine synthase | NCS | SEQ. ID. NO: 400/SEQ. ID. NO: 1261 | 4-Hydroxyphenylacetaldehyde and dopamine/(S)-Norcoclaurine |
| Norcoclaurine 6-O-methyltransferase | 6OMT | SEQ. ID. NO: 726/SEQ. ID. NO: 1672 | (R,S)-Norcauclaurine/(R,S)-Coclaurine |
| Reticuline 7-O-methyltransferase | 7OMT | SEQ. ID. NO: 730/SEQ. ID. NO: 1676 | (R,S)-Reticuline/(R,S)-Norreticuline |
| 3'-Hydroxy-N-methylcoclaurine 4'-O-methyltransferase | 4'OMT | SEQ. ID. NO: 776/SEQ. ID. NO: 1723 | (R,S)-3'-Hydroxy-N-methylcoclaurine/(R,S)-Reticuline |
| Norreticuline 7-O-methyltransferase | N7OMT | SEQ. ID. NO: 621/SEQ. ID. NO: 1567 | (R,S)-Norreticuline/(R,S)-7-O-methylnorreticuline |

TABLE 1-continued

| Enzyme Name | Abbreviation | Exemplary SEQ ID NO (polynucleotide/amino acid) | Exemplary Substrate/Product |
|---|---|---|---|
| Scoulerine 9-O-methyltransferase | SOMT | SEQ. ID. NO: 783/SEQ. ID. NO: 1730 | (S)-Scoulerine/(S)-Tetrahydrocolumbamine |
| Columbamine O-methyltransferase | CoOMT | SEQ. ID. NO: 718/SEQ. ID. NO: 1664 | (S)-Tetrahydrocolumbamine/(S)-tetrahydrodopalmatine |
| Coclaurine-N-methyltransferase | CNMT | SEQ. ID. NO: 446/SEQ. ID. NO: 1304 | (S)-Coclaurine/(S)-N-Methylcoclaurine |
| Tetrahydroprotoberberine cis-N-metyltransferase | TNMT | SEQ. ID. NO: 445/SEQ. ID. NO: 1303 | (S)-Stylopine/(S)-cis-N-Methylstylopine |
| Pavine N-methyltransferase | PavNMT | SEQ. ID. NO: 494 SEQ. ID. NO: 1352 | (+,−)-Pavine/(+/−)-N-Methylpavine |
| Berbamunine synthase | BS, CYP80A1 | SEQ. ID. NO: 98/SEQ. ID. NO: 1009 | (R,S)-N-Methylcoclaurine/Berbamunine |
| Corytuberine synthase | CTS, CYP80A1 | SEQ. ID. NO: 146/SEQ. ID. NO: 1002 | (S)-Reticuline/corytuberine |
| N-Methylcoclaurine 3'-hydroxylase | NMCH, CYP80B3 | SEQ. ID. NO: 137/SEQ. ID. NO: 962 | (S)-N-Methylcoclaurine/(S)-3'-Hydroxy-N-Methylcoclaurine |
| (S)-N-Methylstylopine 14-hydroxylase | MSH, CYP82N4 | SEQ. ID. NO: 147/SEQ.ID. NO: 1012 | (S)-cis-Methylstylopine/Protopine |
| Protopine 6-hydroxylase | P6H, CYP82N3 | SEQ. ID. NO: 176/SEQ. ID. NO: 1041 | Protopine/Dihydrosanguinerine |
| (S)-N-Methylcanadine 1-hydroxylase | NMCanH, CYP82Y1 | SEQ. ID. NO: 214/SEQ. ID. NO: 1079 | (S)-N-Methylcanadine/(S)-1-Hydroxy-N-Methylcanadine |
| Canadine synthase | CAS, CYP719A19 | SEQ. ID. NO: 283/SEQ. ID. NO: 1148 | (S)-Tetrahydrocolumbamine/(S)-Canadine |
| Cheilantofoline synthase | CFS, CYP719A25 | SEQ. ID. NO: 262/SEQ.ID. NO: 1127 | (S)-Scoulerine/(S)-Cheilantofoline |
| Stylopine synthase | SPS, CYP719A20 | SEQ. ID. NO: 264/SEQ. ID. NO: 1129 | (S)-Cheilantofoline/(S)-Stylopine |
| Salutaridine synthase | SalSyn, CYP719B1 | SEQ. ID. NO: 274/SEQ.ID. NO: 1139 | (R)-Reticuline/Salutaridine |
| Salutaridine reductase | SalR | SEQ. ID. NO: 789/SEQ. ID. NO: 1454 | Salutaridine/Salutaridinol |
| Salutaridine 7-O-acetyltransferase | SalAT | SEQ. ID. NO: 579/SEQ. ID. NO: 1443 | Salutaridinol/Thebaine |
| Thebaine 6-O-demethylase | T6ODM | PBRDIOX13 SEQ. ID. NO: 347/SEQ. ID. NO: 1212 | Thebaine/Codeinone |
| Thebaine 6-O-demethylase | T6ODM | PBRDIOX13 SEQ. ID. NO: 347/SEQ. ID. NO: 1212 | Oripavine/Morphinone |
| Codeine O-demethylase | CODM | PBRDIOX12 SEQ. ID. NO: 346/SEQ. ID. NO: 1211 | Codeine/Morphine |
| Codeine O-demethylase | CODM | PBRDIOX12 SEQ. ID. NO: 346/SEQ. ID. NO: 1211 | Thebaine/Oripavine |
| Protoberberine O-dealkylase | PODA | PBRDIOX11 SEQ. ID. NO: 345/SEQ. ID. NO: 1210 | Cryptopine/O-Demethylcryptopine |
| Codeinone reductase | COR | SEQ. ID NO: 34/SEQ. ID. NO: 903 | Codeinone/Codeine |
| Codeinone reductase | COR | SEQ. ID. NO: 34/SEQ. ID. NO: 903 | Morphinone/Morphine |
| Dihydrobenzophenanthridin oxidase | DBOX | SEQ. ID. NO: 373/SEQ. ID. NO: 1235 | Papaverine |
| (S)-Tetrahydroprotoberberine oxidase | STOX | SEQ. ID. NO: 387/SEQ. ID. NO: 1248 | (S)-Canadine/Berberine |
| Sanguinerine reductase | SanR | SEQ. ID. NO: 818/SEQ. ID. NO: 1484 | Sanguinerine/Dihydrosanguinerine |
| Noscapine synthase | NOS | SEQ. ID. NO: 521/SEQ. ID. NO: 1384 | Narcotinehemiacetal/Noscapine |
| 3-O-Acetylpapaveroxine carboxylesterase | CXE1 | SEQ. ID. NO: 562/SEQ. ID. NO: 1426 | 3-O-Acetylpapaveroxine/Narcotinehemiacetal |
| 1,13-Dihydroxy-N-methylcanadine 13-O-acetyltransferase | AT1 | SEQ. ID. NO: 61/SEQ. ID. NO: 930 | 1,13-Dihydroxy-N-methylcanadine/1-Hydroxy-13-O-acetyl-N-methylcanadine |

TABLE 2

| | | | | | Rocha GS-FLX Titanium | | | | | | Intersects between 454 and Illumina predicted full-length CDS |
|---|---|---|---|---|---|---|---|---|---|---|---|
| No. | Abbrev. | Plant | Tissue | SRA accession number | Number of raw reads | Number of cleaned reads | Average read length (bp) | Average transcript read depth (reads/bp) | Unigenes | Predicted full-length CDS | |
| 1 | AME | *Argemone mexicana* | Stem | SRX076322 | 579,575 | 511,923 | 406 | 8.0 | 25,499 | 14,446 | 8,010 |
| 2 | BTH | *Berberis thunbergii* | Root | SRX202153 | 728,069 | 721,524 | 340 | 6.2 | 41,672 | 12,312 | 6,129 |

TABLE 2-continued

| | | | | Rocha GS-FLX Titanium | | | | | | Intersects between 454 and Illumina predicted full-length CDS |
|---|---|---|---|---|---|---|---|---|---|---|
| No. | Abbrev. | Plant | Tissue | SRA accession number | Number of raw reads | Number of cleaned reads | Average read length (bp) | Average transcript read depth (reads/bp) | Unigenes | Predicted full-length CDS | |
| 3 | CMA | Chelidonium majus | Stem | SRS150402 | 504,849 | 406,742 | 347 | 7.1 | 23,678 | 10,312 | 8,296 |
| 4 | CMU | Cissampelos mucronata | Callus | SRX130678 | 721,691 | 714,978 | 376 | 7.3 | 35,166 | 14,300 | 9,877 |
| 5 | CTR | Cocculus trilobus | Callus | SRX130662 | 535062 | 625,283 | 327 | 5.2 | 34,783 | 11,784 | 127 |
| 6 | CCH | Corydalis chelanthifolia | Root | SRX078320 | 502,500 | 431,507 | 360 | 7.6 | 22,511 | 10,912 | 8,716 |
| 7 | ECA | Eschscholzia californica | Root | SRS160613 | 472,167 | 423,743 | 428 | 5.6 | 32,160 | 17,365 | 12,911 |
| 8 | GFL | Glaucium flavum | Root | SRS212395 | 648,604 | 540,433 | 396 | 8.1 | 26,520 | 12,084 | 8,199 |
| 9 | HCA | Hydrastis canadensis | Rhizome | SRS212407 | 685,239 | 440,063 | 254 | 8.8 | 23,809 | 10,801 | 7,617 |
| 10 | JDI | Jeffersonnia diphylla | Root | SRX202161 | 833,182 | 821,875 | 340 | 7.4 | 38,773 | 13,293 | 8,680 |
| 11 | MAQ | Mahonia aquifolium | Bark | SRX078960 | 506,160 | 442,484 | 289 | 5.1 | 36,429 | 11,802 | 495 |
| 12 | MCA | Menispermum canadense | Rhizome | SRX078321 | 443,738 | 392,619 | 378 | 5.7 | 36,399 | 8,858 | 3,956 |
| 13 | NDA | Nandina domestica | Root | SRX202162 | 832,375 | 821,728 | 372 | 6.4 | 45,387 | 18,367 | 11,138 |
| 14 | NSA | Nigella sativa | Root | SRX078325 | 1,326,496 | 1,203,320 | 318 | 9.1 | 50,508 | 19,551 | 10,457 |
| 15 | PBR | Papaver bracteatum | Stem | SRS180614 | 595,176 | 528,920 | 360 | 4.7 | 46,224 | 18,879 | 14,042 |
| 16 | SCA | Sanguinaria canadensis | Rhizome | SRS212403 | 653,689 | 571,622 | 417 | 6.7 | 25,652 | 11,787 | 9,514 |
| 17 | SDI | Stylophorum diphyllum | Stem | SRX078312 | 846,959 | 576,700 | 353 | 5.5 | 43,568 | 19,631 | 9,636 |
| 18 | TFL | Thalictrum flavum | Root | SRX039636 | 440,689 | 401,315 | 385 | 7.8 | 21,146 | 13,002 | 8,153 |
| 19 | TCO | Tinospora cordifolia | Callus | SRX130689 | 647,850 | 641,837 | 381 | 6.8 | 34,518 | 14362 | 9,403 |
| 20 | XSI | Xanthoriza simplicissima | Rhizome | SRX078324 | 978,176 | 729,767 | 265 | 6.3 | 42,969 | 15,995 | 7,107 |
| | | Average | | | 664,213 | 592,535 | 356 | 6.8 | 34,368 | 13,993 | 7,708 |

TABLE 3

| | | | | Illumina GA/HiSeq | | | | | |
|---|---|---|---|---|---|---|---|---|---|
| No. | Abbrev. | Plant | Tissue | SRA accession number | Number of raw reads | Number of cleaned reads | Average transcript read depth (reads/bp) | Unigenes | Predicted full-length CDS |
| 1 | AME | Argemone mexicana | Stem | SRX096074 | 79,936,080 | 50,819,736 | 39.1 | 75,101 | 32,940 |
| 2 | BTH | Berberis thunbergii | Root | SRX096075 | 70,074,022 | 64,584,658 | 53.1 | 88,302 | 24976 |
| 3 | CMA | Chelidonium majus | Stem | SRX096034 | 62,362,800 | 50,819,736 | 32.3 | 45,005 | 32,416 |
| 4 | CMU | Cissampelos mucronata | Callus | SRX130854 | 232,997,416 | 190,922,766 | 137.1 | 69,822 | 21,140 |
| 5 | CTR | Cocculus trilobus | Callus | SRX202432 | 220,956,972 | 190,682,284 | 69.0 | 84,793 | 3,773 |
| 6 | CCH | Corydalis chelanthifolia | Root | SRX096066 | 79,161,120 | 69073478 | 38.2 | 51,797 | 42,019 |
| 7 | ECA | Eschscholzia californica | Root | SRX096037 | 62,704,080 | 53,746,798 | 37.3 | 42,167 | 31,085 |
| 8 | GFL | Glaucium flavum | Root | SRX096058 | 60,410,640 | 38,697,818 | 63.2 | 31,100 | 15,861 |
| 9 | HCA | Hydrastis canadensis | Rhizome | SRX096072 | 71,077,680 | 61,254,386 | 87.8 | 33,335 | 18,744 |
| 10 | JDI | Jeffersonia diphylla | Root | SRX202488 | 331915850 | 235,742,972 | 187.5 | 86,832 | 24,421 |
| 11 | MAQ | Mahonia aquifolium | Bark | SRX202767 | 231932044 | 196,915,558 | 62.2 | 98,375 | 13,866 |
| 12 | MCA | Menispermum canadense | Rhizome | SRX096076 | 82,491,120 | 71,509,392 | 42.7 | 87,141 | 32,954 |
| 13 | NDA | Nandina domestica | Root | SRX096070 | 84,144,000 | 70,453,764 | 51.9 | 70,425 | 27,337 |
| 14 | NSA | Nigella sativa | Root | SRX096077 | 76517332 | 70,223,386 | 56.3 | 67,591 | 22,508 |
| 15 | PBR | Papaver bracteatum | Stem | SRX096061 | 69721200 | 57,768,096 | 36.0 | 70,428 | 37,752 |
| 16 | SCA | Sanguinaria canadensis | Rhizome | SRX096071 | 71,713,920 | 59,322,808 | 23.3 | 53,019 | 37,241 |
| 17 | SDI | Stylophorum diphyllum | Stem | SRX096064 | 70,502,640 | 52,300,928 | 59.5 | 50,125 | 18,970 |
| 18 | TFL | Thalictrum flavum | Root | SRX096062 | 66,080,640 | 49,761,080 | 79.6 | 41,982 | 15,426 |
| 19 | TCO | Tinospora cordifolia | Callus | SRX202768 | 238,046,752 | 195,094,516 | 142.6 | 81,927 | 18,967 |
| 20 | XSI | Xanthoriza simplicissima | Rhizome | SRX245855 | 67,378,080 | 59,166,962 | 93.4 | 48,447 | 16,436 |
| | | Average | | | 116,506,219 | 94,443,056 | 69.6 | 63,886 | 24,442 |

TABLE 4

| No. | Abbrev. | Plant | Rocha GS-FLX Titanium | | | | | Illumina GA/HiSeq | | | | |
|---|---|---|---|---|---|---|---|---|---|---|---|---|
| | | | Unigenes | Overall annotated | High-level annotated | GO annotated | EC number allocated | Unigenes | Overall annotated | High-level annotated | GO annotated | EC number allocated |
| 1 | AME | *Argemone mexicana* | 25,499 | 22,121 | 17,979 | 21,974 | 3,086 | 75,101 | 60,836 | 45,404 | 60,254 | 7,653 |
| 2 | BTH | *Berberis thunbergii* | 41,672 | 33,548 | 23,243 | 33,080 | 4,197 | 68,302 | 61,576 | 41,927 | 60,561 | 7,289 |
| 3 | CMA | *Chelidonium majus* | 23,878 | 19,635 | 13,977 | 19,460 | 2,368 | 45,005 | 42,057 | 33,449 | 41,956 | 6,092 |
| 4 | CMU | *Cissampelos mucronata* | 35,166 | 27,451 | 19,865 | 27,139 | 3,147 | 69,622 | 32,209 | 22,943 | 31,597 | 3,314 |
| 5 | CTR | *Cocculus trilobus* | 34,783 | 26,678 | 18,701 | 28,338 | 3,197 | 84,793 | 33,055 | 21,961 | 30,542 | 432 |
| 6 | CCH | *Corydalis chelanthifolia* | 22,511 | 19,161 | 14,633 | 19,024 | 2,433 | 51,797 | 46,423 | 42,764 | 48,139 | 7,738 |
| 7 | ECA | *Eschscholzia californica* | 32,150 | 26,430 | 21,403 | 28,194 | 4,221 | 42,167 | 38,332 | 32,677 | 38,063 | 6,545 |
| 8 | GFL | *Glaucium flavum* | 26,520 | 20,945 | 15,645 | 20,725 | 2,719 | 31,100 | 31,100 | 19,669 | 31,100 | 3,231 |
| 9 | HCA | *Hydrastis canadensis* | 23,809 | 20,443 | 15,491 | 20,230 | 2,511 | 33,335 | 33,335 | 20,896 | 33,335 | 3,637 |
| 10 | JDI | *Jeffersonnia diphylla* | 36,773 | 24,583 | 16,777 | 24,199 | 2,581 | 86,832 | 31,712 | 22,574 | 30,842 | 3,116 |
| 11 | MAQ | *Mahonia aquifolium* | 36,429 | 30,209 | 20,624 | 29,805 | 3,581 | 98,375 | 53,093 | 33,434 | 47,040 | 621 |
| 12 | MCA | *Menispermum canadense* | 36,399 | 31,715 | 24,565 | 31,482 | 4,495 | 87,141 | 70,524 | 52,713 | 69,877 | 8,924 |
| 13 | NDA | *Nandina domestica* | 45,387 | 33,501 | 24,308 | 33,010 | 4,186 | 70,425 | 53,109 | 38,428 | 52,531 | 6,553 |
| 14 | NSA | *Nigella sativa* | 60,506 | 36,231 | 25,560 | 35,591 | 4,526 | 67,591 | 41,260 | 29,127 | 40,316 | 4,807 |
| 15 | PBR | *Papaver bracteatum* | 48,224 | 33,168 | 24,381 | 32,767 | 4,988 | 70,428 | 56,483 | 37,334 | 53,039 | 6,793 |
| 16 | SCA | *Sanguinaria canadensis* | 25,652 | 20,493 | 15,938 | 20,301 | 2,621 | 53,019 | 47,247 | 40,122 | 46,890 | 7,715 |
| 17 | SDI | *Stylophorum diphyllum* | 43,568 | 34,954 | 26,144 | 34,614 | 5,115 | 50,125 | 40,797 | 30,157 | 40,324 | 5,276 |
| 18 | TFL | *Thalictrum flavum* | 21,146 | 17,609 | 12,121 | 17,431 | 2,294 | 41,962 | 33,120 | 23,900 | 32,711 | 4,123 |
| 19 | TCO | *Tinospora cordifolia* | 34,518 | 28,044 | 21,199 | 27,795 | 3,444 | 81,927 | 35,851 | 24,174 | 34,712 | 3,386 |
| 20 | XSI | *Xanthoriza simplicissima* | 42,969 | 33,657 | 22,165 | 33,187 | 3,740 | 48,447 | 39,281 | 27,434 | 38,831 | 4,642 |
| | | Average | 34,368 | 27,128 | 19,736 | 28,817 | 3,472 | 63,886 | 44,169 | 32,055 | 43,133 | 5,089 |

TABLE 5

| Substrate | Enzyme | | | | | | |
|---|---|---|---|---|---|---|---|
| | GFLOMT1 | GFLOMT2 | GFLOMT3 | GFLOMT4 | GFLOMT5 | GFLOMT6 | GFLOMT7 |
| (R,S)-Norlaudanosoline | 96 | 100 | nd | nd | nd | nd | nd |
| (R,S)-6-O-Methylnorlaudanosoline | 87 | 1 | nd | nd | nd | nd | nd |
| (R,S)-6-O-Methyllaudanosoline | 68 | 14 | nd | nd | nd | 23 | nd |
| (R,S)-Norreticuline | nd | nd | nd | nd | nd | 36 | nd |
| (S)-Reticuline | 6 | 22 | nd | nd | nd | 97 | nd |
| (R,S)-Scoulerine | 32 | 75 | nd | nd | nd | 100 | 12 |
| (R,S)-Tetrahydrocolubamine | 19 | 32 | nd | nd | nd | 91 | 8 |

TABLE 6

| Compound | [M + H]+ or [M]+ | RT (min) | CE (eV) | ESI-CID spectrum m/z (relative intensity) | Reference |
|---|---|---|---|---|---|
| Norlaudanosoline [1] | 288 | 2.20 | 30 | 288 (1), 164 (60), 161 (14), 143 (40), 137 (5), 123 (100), 115 (25), 91 (5) | Authentic standard |
| 6-O-Methylnorlaudanosoline [2] | 302 | 2.64 | 30 | 207 (9), 179 (8), 178 (56), 175 (12), 163 (16), 160 (9), 143 (51), 137 (10), 123 (100), 115 (18) | Authentic standard |

TABLE 6-continued

| Compound | [M + H]+ or [M]+ | RT (min) | CE (eV) | ESI-CID spectrum m/z (relative intensity) | Reference |
|---|---|---|---|---|---|
| 6-O-Methyllaudanosoline [3] | 316 | 2.62 | 30 | 207 (9), 192 (52), 179 (8), 178 (6), 177 (19), 175 (16), 161 (5), 160 (10), 143 (48), 137 (17), 123 (100), 115 (15), 91 (5) | Authentic standard |
| Norreticuline [4] | 316 | 2.95 | 30 | 239 (5), 207 (9), 179 (8), 178 (100), 175 (11), 163 (30), 160 (10), 151 (6), 143 (48), 137 (72), 121 (8), 119 (5), 115 (19), 91 (5) | Authentic standard |
| Scoulerine [5] | 328 | 3.08 | 30 | 178 (100), 163 (19), 151 (10), 119 (5) | Authentic standard |
| Reticuline [6] | 330 | 2.98 | 30 | 207 (8), 192 (100), 179 (6), 177 (36), 175 (15), 160 (8), 151 (7), 143 (47), 137 (81), 115 (13) | Authentic standard |
| Norlaudanine [7] | 330 | 3.25 | 25 | 330 (2), 313 (2), 298 (2), 281 (6), 266 (2), 253 (5), 241 (2), 229 (2), 206 (2), 192 (100), 178 (57), 165 (3), 151 (22), 143 (5), 137 (28) | Desgagne-Penix and Facchini, 2012 |
| Tetrahydrocolumbine [8] | 342 | 3.32 | 30 | 178 (100), 163 (18), 151 (6) | Authentic standard |
| Codamine [9] | 344 | 3.15 | 25 | 344 (1), 253 (2), 192 (100), 175 (7), 151 (24), 143 (17), 137(2) | Desgagne-Penix and Facchini, 2012 |
| Laudanine [10] | 344 | 3.24 | 25 | 344 (3), 313 (7), 298 (3), 282 (3), 267 (1), 253 (4), 206 (100), 192 (23), 189 (51), 175 (5), 174 (10), 158 (1), 151 (22), 143 (1), 137 (52) | Schmidt et al, 2007 |
| Tetrahydropapaverine [11] | 344 | 3.42 | 30 | 296 (6), 281 (8), 192 (100), 189 (24), 177 (12), 176 (9), 174 (29), 165 (6), 159 (13), 158 (30), 151 (89), 148 (6), 144 (5) | Authentic standard |
| Tetrahydropalmatine [12] | 356 | 3.61 | 30 | 192 (100), 177 (6), 176 (5), 165 (15), 150 (9) | Authentic standard |
| Laudanosine [13] | 358 | 3.40 | 25 | 358 (3), 327 (3), 312 (1), 296 (4), 206 (100), 189 (34), 174 (10), 165 (8), 158 (5), 151 (29), 44 (1) | Schmidt et al, 2007 |

TABLE 7

| Recombinant Enzyme | Substrate | Product(s) | [M + H]+ or [M]+ | RT (min) | CE (eV) | ESI[+]-CID spectrum of product m/z (relative intensity) | Number of isoquinoline (I) or benzyl (B) methyl groups |
|---|---|---|---|---|---|---|---|
| GFLOMT1 | Norlaudanosoline | 6-O-Methyl-norlaudanosoline [2] | 302 | 2.62 | 30 | 207 (8), 179 (10), 178 (53), 175 (7), 164 (12), 163 (17), 160 (8), 143 (47), 137 (19), 123 (100), 115 (23) | I: 1 |
| | | Norreticuline [4] | 316 | 2.95 | 30 | 207 (6), 179 (5), 178 (100), 175 (9), 163 (28), 160 (6), 143 (50), 137 (73), 122 (67), 115 (16) | I: 1, B: 1 |
| | 6-O-Methyl-norlaudanosoline | Norreticuline [4] | 316 | 2.95 | 30 | 207 (7), 179 (5), 178 (100), 175 (7), 163 (30), 160 (7), 143 (46), 137 (78), 122 (7), 115 (21) | I: 1, B: 1 |
| | | Norcodamine [14] | 330 | 3.15 | 30 | 178 (100), 175 (9), 163 (26), 151 (53), 143 (45), 115 (9) | I: 1, B: 2 |
| | 6-O-Methyl-laudanosoline | Reliculine [6] | 330 | 2.99 | 30 | 207 (6), 192 (100), 177 (26), 175 (15), 160 (7), 151 (6), 143 (36), 137 (68), 115 (8) | I: 2, B: 1 |
| | | Codamine [9] | 344 | 3.17 | 30 | 192 (100), 177 (19), 175 (6), 151 (44), 143 (39) | I: 2, B: 2 |
| | Reticuline | Codamine [9] | 344 | 3.15 | 30 | 192 (100), 175 (10), 151 (45), 143 (33), 137 (6), 115 (5) | I: 2, B: 2 |
| | Scoulerine | Tetrahydro-palmatrubine [15] | 342 | 3.42 | 30 | 192 (100), 177 (5), 176 (7), 165 (18), 150 (10) | I: 2, B: 1 |
| | | Tetrohydro-palmaline [12] | 356 | 3.62 | 30 | 192 (100), 177 (6), 176 (6), 165 (18), 150 (8) | I: 2, B: 2 |
| | Tetrohydro-columbamine | Tetrahydro-palmatine [12] | 356 | 3.62 | 30 | 192 (100), 177 (6), 176 (6), 165 (18), 150 (8) | I: 2, B: 2 |
| GFLOMT2 | Norlaudanosoline | 6-O-Methyl-norlaudanosoline [2] | 302 | 2.64 | 30 | 207 (10), 179 (10), 178 (61), 175 (12), 163 (16), 160 (9), 143 (52), 137 (10), 123 (100), 115 (17) | I: 1 |

TABLE 7-continued

| Recombinant Enzyme | Substrate | Product(s) | [M + H]+ or [M]+ | RT (min) | CE (eV) | ESI[+]-CID spectrum of product m/z (relative intensity) | Number of isoquinoline (I) or benzyl (B) methyl groups |
|---|---|---|---|---|---|---|---|
| | 6-O-Methyl-norlaudanosoline | Nororientaline [16] | 316 | 2.88 | 30 | 239 (6), 224 (5), 207 (5), 178 (100), 175 (10), 163 (12), 160 (14), 143 (91), 137 (98), 115 (11) | I: 1, B: 1 |
| | 6-O-Methyl-laudanosoline | Orientaline [17] | 330 | 2.85 | 30 | 207 (8), 192 (100), 178 (6), 177 (25), 175 (19), 160 (7), 151 (9), 143 (60), 137 (93), 115 (9), 91 (5) | I: 2, B: 1 |
| | | Reticuline [6] | 330 | 2.98 | 30 | 192 (100), 177 (28), 175 (17), 160 (7), 151 (6), 143 (43), 137 (60), 115 (7) | I: 2, B: 1 |
| | | Codamine [9] | 344 | 3.15 | 30 | 192 (100), 177 (18), 175 (7), 151 (31), 143 (25) | I: 2, B: 2 |
| | Reliculine | Codamine [9] | 344 | 3.18 | 30 | 192 (100), 177 (17), 175 (9), 151 (39), 143 (29) | I: 2, B: 2 |
| | Scoulerine | Tetrahydro-palmatrubine [15] | 342 | 3.43 | 30 | 192 (100), 177 (6), 165 (26), 150 (11) | I: 2, B: 1 |
| | | Tetrahydro-palmatine [12] | 356 | 3.61 | 30 | 192 (100), 177 (9), 176 (13), 165 (31), 150 (11) | I: 2, B: 2 |
| | Tetrohydro-columbamine | Tetrohydro-palmatine [12] | 356 | 3.59 | 30 | 192 (100), 177 (5), 165 (15), 150 (7) | I: 2, B: 2 |
| GFLOMT6 | 6-O-Methyl-laudanosoline | 6,7-O,O-Dimethyl-laudanosoline [18] | 330 | 2.87 | 30 | 284 (7), 206 (40), 192 (16), 190 (9), 189 (30), 177 (10), 175 (6), 174 (17), 161 (9), 159 (5), 158 (19), 151 (11), 143 (17), 137 (26), 123 (100), 91 (6) | I: 3 |
| | Norreticuline | Norcodamine [14] | 330 | 3.16 | 30 | 178 (100), 163 (25), 151 (60), 143 (52), 115 (12) | I: 1, B: 2 |
| | | Norlaudanine [7] | 330 | 3.25 | 30 | 222 (9), 192 (100), 189 (11), 187 (13), 178 (13), 177 (16), 176 (10), 174 (13), 165 (8), 159 (16), 158 (10), 151 (8), 145 (11), 143 (20), 137 (91), 115 (5) | I: 2, B: 1 |
| | | Tetrahydro-papaverine [11] | 344 | 3.43 | 30 | 295 (5), 193 (6), 192 (100), 191 (82), 189 (10), 177 (15), 174 (36), 159 (14), 151 (77), 136 (11), 107 (10) | I: 2, B: 2 |
| | Reticuline | Codamine [9] | 344 | 3.17 | 30 | 192 (100), 177 (27), 175 (9), 160.3 (6), 151 (42), 143 (33), 115 (6) | I: 2, B: 2 |
| | | Laudanine [10] | 344 | 3.24 | 30 | 282 (6), 267 (5), 206 (98), 192 (8), 191 (15), 190 (11), 189 (29), 175 (6), 174 (24), 159 (6), 158 (21), 151 (28), 143 (7), 137 (100), 91 (5) | I: 3, B: 1 |
| | | Laudanosine [13] | 358 | 3.43 | 30 | 296 (6), 281 (5), 206 (100), 191 (9), 190 (9), 189 (31), 174 (23), 165 (11), 159 (5), 158 (18), 151 (68), 150 (5) | I: 3, B: 2 |
| | Scoulerine | Tetrahydro-columbine [8] | 342 | 3.29 | 30 | 178 (100), 163 (13), 151 (6) | I: 1, B: 2 |
| | | Tetrahydro-palmatine [12] | 356 | 3.59 | 30 | 192 (100), 177 (5), 165 (16), 150 (8) | I: 2, B: 2 |
| | Tetrahydro-columbamine | Tetrahydro-palmatine [12] | 356 | 3.6 | 30 | 192 (100), 177 (5), 165 (20), 150 (9) | I: 2, B: 2 |
| GFLOMT7 | Scoulerine | Tetrahydro-columbamine [8] | 342 | 3.33 | 30 | 178 (100), 163 (15), 151 (5) | I: 1, B: 2 |
| | | Tetrahydro-palmatrubine [15] | 342 | 3.44 | 30 | 192 (100), 190 (5), 177 (5), 165 (21), 150 (11) | I: 2, B: 1 |
| | Tetrohydro-columbamine | Tetrohydro-palmatine [12] | 356 | 3.62 | 30 | 192 (100), 165 (15), 150 (10) | I: 2, B: 2 |

REFERENCES

Caniard, A., Zerbe, P., Legrand, S., Cohade, A., Valot, N., Magnard, J.-L., Bohlmann, J., Legendre, L. 2012. Discovery and functional characterization of two diterpene synthases for sclareol biosynthesis in *salvia sclarea* (L.) and their relevance for perfume manufacture. BMC Plant Biology 12, 119.

Chevreux, B., Pfisterer, T., Drescher, B., Driesel, A. J., Müller, W. E., Wetter, T., Suhai, S. 2004. Using the miraEST assembler for reliable and automated mRNA transcript assembly and SNP detection in sequenced ESTs. Genome Resource 14, 1147-1159.

Chomczynski, P., Sacchi, N. 1987. Single-step method of RNA isolation by acid guanidinium thiocyanate-phenol-chloroform extraction. Analytical Biochemistry 162, 156-159.

Desgagne-Penix, I., Khan, M. F., Schriemer, D. C., Cram, D., Nowak, J., Facchini, P. J. 2010. Integration of deep transcriptome and proteome analyses reveals the components of alkaloid metabolism in opium poppy cell cultures. BMC Plant Biology 10, 252.

Fossati, E., Ekins, A., Narcross, L., Zhu, Y., Falgueyret, J. P., Beaudoin, G. A., Facchini, P. J., Martin, V. J. 2014. *Reconstitution of a 10-gene pathway for synthesis of the plant alkaloid dihydrosanguinarine in Saccharomyces cerevisiae*. Nature Communications 5, 3283.

Gaasterland, T., Sensen, C. W. 1996. MAGPIE: automated genome interpretation. Trends in Genetics 12, 76-78.

Hawkins, K. M., Smolke, C. D. 2008. Production of benzylisoquinoline alkaloids in *Saccharomyces cerevisiae*. Nature Chemical Biology 4, 564-573.

Huang, X., Madan, A. 1999. CAP3: A DNA sequence assembly program. Genome Research 9, 868-877.

Iseli, C., Jongeneel, C. V., Bucher, P. 1999. ESTScan: a program for detecting, evaluating, and reconstructing potential coding regions in EST sequences. Proceedings of the 7th International Conference on Intelligent Systems for Molecular Biology 7, 138-148.

Jurka, J., Kapitonov, V. V., Pavlicek, A., Klonowski, P., Kohany, O., Walichiewicz, J. 2005. Repbase Update, a database of eukaryotic repetitive elements. Cytogenetic and Genome Research 110, 462-467.

Langmead, B., Trapnell, C., Pop, M., Salzberg, S. L. 2009. Ultrafast and memory-efficient alignment of short DNA sequences to the human genome. Genome Biology 10, R25.

Li, B., Dewey, C. N. 2011. RSEM: accurate transcript quantification from RNA-Seq data with or without a reference genome. BMC Bioinformatics 12, 323.

Li, W., Godzik, A. 2006. Cd-hit: a fast program for clustering and comparing large sets of protein or nucleotide sequences. Bioinformatics 22, 1658-1659.

Liscombe, D. K., Ziegler, J., Schmidt, J., Ammer, C., Facchini, P. J. 2009. Targeted metabolite and transcript profiling for elucidating enzyme function: isolation of novel N-methyltransferases from three benzylisoquinoline alkaloid-producing species. Plant Journal 60, 729-743.

Lottaz, C., Iseli, C., Jongeneel, C. V., Bucher, P. 2003. Modeling sequencing errors by combining hidden Markov models. Bioinformatics 19, ii103-112.

Martin, V. J. J., Pitera, D. J., Withers, S. T., Newman, J. D., Keasling, J. D. 2003. Engineering a mevalonate pathway in *Escherichia coli* for production of terpenoids. Nature Biotechnology 21, 796-802.

Martin, J. A., Wang, Z. 2011. Next-generation transcriptome assembly. Nature Reviews Genetics 12, 671-682.

Metzker, M. L. 2010. Sequencing technologies—the next generation. Nature Reviews Genetics 11, 31-46.

Minami, H., Kim, J. S., Ikezawa, N., Takemura, T., Katayama, T., Kumagai, H., Sato, F. 2008. Microbial production of plant benzylisoquinoline alkaloids. Proceedings of the National Academy of Sciences of the United States of America 105, 7393-7398.

Nakagawa. A., Minami, H., Kim. J. S., Koyanagi, T., Katayama. T., Sato. F., Kumagai, H. 2011. A bacterial platform for fermentative production of plant alkaloids. Nature Communications 2, 326.

Nakamura, K., Oshima, T., Morimoto, T., Ikeda, S., Yoshikawa, H., Shiwa, Y., Ishikawa, S., Linak, M. C., Hirai, A., Takahashi, H., Altaf-Ul-Amin Md., Ogasawara, N., Kanaya, S. 2011. Sequence-specific error profile of Illumina sequencers. Nucleic acids research 39: e90.

Novák, V., Slavík, J. 1974. Further alkaloids from *Glaucium flavum* CR. Collection of Czechoslovak Chemical Communications 39, 3352-3356.

Ouyang, S., Buell, C. R. 2004. The TIGR Plant Repeat Databases: a collective resource for the identification of repetitive sequences in plants. Nucleic Acids Research 32, D360-363.

Pruesse, E., Quast, C., Knittel, K., Fuchs, B. M., Ludwig, W., Peplies, J., Glöckner, F. O. 2007. SILVA: a comprehensive online resource for quality checked and aligned ribosomal RNA sequence data compatible with ARB. Nucleic Acids Research 35, 7188-7196.

Pruitt, K. D., Tatusova, T., Maglott, D. R. 2007. NCBI reference sequences (RefSeq): acurated non-redundant sequence database of genomes, transcripts and proteins. Nucleic Acids Research 35, D61-65.

Ro, D. K., Paradise, E. M., Ouellet, M., Fisher, K. J., Newman, K. L., Ndungu, J. M., Ho, K. A., Eachus, R. A., Ham, T. S., Kirby, J., Chang, M. C., Withers, S. T., Shiba, Y., Sarpong, R., Keasling, J. D. 2006. Production of the antimalarial drug precursor artemisinic acid in engineered yeast. Nature 440, 940-943.

Zhang, Z., Schwartz, S., Wagner, L., Miller, W. 2000. A greedy algorithm for aligning DNA sequences. Journal of Computational Biology 7, 203-214.

Zerbe, P., Chiang, A., Yuen, M., Hamberger, B., Hamberger, B., Draper, J. A., Britton, R., Bohlmann, J. 2012. Bifunctional cis-abienol synthase from *Abies balsamea* discovered by transcriptome sequencing and its implications for diterpenoid fragrance production. Journal of Biological Chemistry 287, 12121-12131.

Zerbino, D. R., Birney, E. 2008. Velvet: algorithms for de novo short read assembly using de Bruijn graphs. Genome Research 18, 821-829.

Ziegler, J., Facchini, P. J. 2008. Alkaloid biosynthesis: metabolism and trafficking. Annual Review of Plant Biology 59, 735-769.

SEQUENCE LISTING

The patent application contains a lengthy "Sequence Listing" section. A copy of the "Sequence Listing" is available in electronic form from the USPTO web site (seqdata.uspto.gov/?pageRequest=docDetail&DocID=US20170058305A1). An electronic copy of the "Sequence Listing" will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10487345B2). An electronic copy of the "Sequence Listing" will also be available from the USPTO upon request and payment of the fee set forth in 37 CFR 1.19(b)(3).

The invention claimed is:

1. A method of producing sanguinarine in a yeast host cell, the method comprising:
   (a) providing a yeast host cell that expresses the enzymes *Papaver somniferum* 6-O-methyltransferase (6OMT), *Papaver somniferum* coclaurine-N-methyltransfersase (CNMT), *Papaver somniferum* 4'-O-methyltransferase 2 (4'OMT2), *Papaver somniferum* berberine bridge enzyme (BBE), cheilanthifoline synthase (CFS), *Papaver somniferum* stylopine synthase (SPS), *Papaver somniferum* tetrahydroprotoberberine cis-N-methyltransfersase (TNMT), *Papaver somniferum* (S)-cis-N-methylstylopine-14-hydroxylase (MSH), *Papaver somniferum* protopine 6-hydroxylase (6PH) and *Papaver somniferum* dihydrobenzoreductase (DBOX), and wherein the cheilanthifoline synthase is encoded by SEQ ID NO: 262, and
   (b) growing the yeast cell to produce sanguinarine.

2. A method of producing sanguinarine in a yeast host cell, the method comprising:
   (a) providing a yeast cell that expresses the enzymes *Papaver somniferum* 6-O-methyltransferase (6OMT), *Papaver somniferum* coclaurine-N-methyltransfersase (CNMT), *Papaver somniferum* 4'-O-methyltransferase 2 (4'OMT2), *Papaver somniferum* berberine bridge enzyme (BBE), *Papaver somniferum* cheilanthifoline synthase (CFS), stylopine synthase (SPS), *Papaver somniferum* tetrahydroprotoberberine cis-N-methyltransfersase (TNMT), *Papaver somniferum* (S)-cis-N-methylstylopine-14-hydroxylase (MSH), *Papaver somniferum* protopine 6-hydroxylase (6PH) and *Papaver somniferum* dihydrobenzoreductase (DBOX), and wherein the stylopine synthase (SPS) is encoded by SEQ ID NO: 264, and
   (b) growing the yeast cell to produce sanguinarine.

3. A method of producing sanguinarine in a yeast host cell, the method comprising:
   (a) providing a yeast host cell that expresses the enzymes *Papaver somniferum* 6-O-methyltransferase (6OMT), *Papaver somniferum* coclaurine-N-methyltransfersase (CNMT), *Papaver somniferum* 4'-O-methyltransferase 2 (4'OMT2), *Papaver somniferum* berberine bridge enzyme (BBE), cheilanthifoline synthase (CFS), stylopine synthase (SPS), *Papaver somniferum* tetrahydroprotoberberine cis-N-methyltransfersase (TNMT), *Papaver somniferum* (S)-cis-N-methylstylopine-14-hydroxylase (MSH), *Papaver somniferum* protopine 6-hydroxylase (6PH) and *Papaver somniferum* dihydrobenzoreductase (DBOX), and wherein the cheilanthifoline synthase (CFS) is encoded by SEQ ID NO: 262 and the stylopine synthase (SPS) is encoded by SEQ ID NO: 264, and
   (b) growing the yeast cell to produce sanguinarine.

4. The method according to claim 1, wherein the yeast cell is a *Saccharomyces* cell.

5. The method according to claim 2, wherein the yeast cell is a *Saccharomyces* cell.

6. The method according to claim 4, wherein the *Saccharomyces* cell is a *Saccharomyces cerevisiae* cell.

7. The method according to claim 5, wherein the *Saccharomyces* cell is a *Saccharomyces cerevisiae* cell.

8. The method according to claim 3, wherein the yeast cell is a *Saccharomyces* cell.

9. The method according to claim 8, wherein the *Saccharomyces* cell is a *Saccharomyces cerevisiae* cell.

10. A method of producing sanguinarine in a *Saccharomyces cerevisiae* cell, the method comprising:
    (a) providing a *Saccharomyces cerevisiae* cell that expresses the enzymes 6-O-methyltransferase (6OMT), coclaurine-N-methyltransfersase (CNMT), 4'-O-methyltransferase 2 (4'OMT2), berberine bridge enzyme (BBE), cheilanthifoline synthase (CFS), stylopine synthase (SPS), tetrahydroprotoberberine cis-N-methyltransfersase (TNMT), (S)-cis-N-methylstylopine-14-hydroxylase (MSH), protopine 6-hydroxylase (6PH) and dihydrobenzoreductase (DBOX), and wherein the cheilanthifoline synthase (CFS) is encoded by SEQ ID NO: 262 and is non-homologous to the other enzymes, and
    (b) growing the *Saccharomyces cerevisiae* cell to produce sanguinarine wherein sanguinarine is produced in the cell at a level that is in excess of the level of sanguinarine produced when a homologous CFS is used.

11. A method of producing sanguinarine in a *Saccharomyces cerevisiae* cell, the method comprising:
    (a) providing a *Saccharomyces cerevisiae* cell that expresses the enzymes 6-O-methyltransferase (6OMT), coclaurine-N-methyltransfersase (CNMT), 4'-O-methyltransferase 2 (4'OMT2), berberine bridge enzyme (BBE), cheilanthifoline synthase (CFS), stylopine synthase (SPS), tetrahydroprotoberberine cis-N-methyltransfersase (TNMT), (S)-cis-N-methylstylopine-14-hydroxylase (MSH), protopine 6-hydroxylase (6PH) and dihydrobenzoreductase (DBOX), and wherein the stylopine synthase (SPS) is encoded by SEQ ID NO: 264 and is non-homologous to the other enzymes, and
    (b) growing the *Saccharomyces cerevisiae* cell to produce sanguinarine wherein sanguinarine is produced in the cell at a level that is in excess of the level of sanguinarine produced when a homologous SPS is used.

12. A method of producing sanguinarine in a *Saccharomyces cerevisiae* cell, the method comprising:
    (a) providing a *Saccharomyces cerevisiae* cell that expresses the enzymes 6-O-methyltransferase (6OMT), coclaurine-N-methyltransfersase (CNMT), 4'-O-methyltransferase 2 (4'OMT2), berberine bridge enzyme (BBE), cheilanthifoline synthase (CFS), stylopine synthase (SPS), tetrahydroprotoberberine cis-N-methyltransfersase (TNMT), (S)-cis-N-methylstylopine-14-hydroxylase (MSH), protopine 6-hydroxylase (6PH) and dihydrobenzoreductase (DBOX), and wherein the cheilanthifoline synthase is encoded by SEQ ID NO: 262 and the stylopine synthase (SPS) is encoded by SEQ ID NO: 264 and both the CFS and SPS are non-homologous to the other enzymes, and (b) growing the *Saccharomyces cerevisiae* cell to produce sanguinarine wherein sanguinarine is produced in the cell at a level that is in excess of the level of sanguinarine produced when a homologous CFS and SPS is used.

\* \* \* \* \*